(12) United States Patent  
Tsuruhami et al.

(10) Patent No.: US 7,118,895 B2  
(45) Date of Patent: Oct. 10, 2006

(54) PROCESS FOR PRODUCING AGLYCON BY USING DIGLYCOSIDASE AND FLAVOR-IMPROVED FOOD CONTAINING THE AGLYCON AND CONVERTING AGENT TO BE USED IN THE PROCESS

(75) Inventors: Kazutaka Tsuruhami, Kakamigahara (JP); Atsuki Toumoto, Kakamigahara (JP); Masataka Goto, Kakamigahara (JP); Satoshi Koikeda, Kakamigahara (JP)

(73) Assignee: Amano Enzyme Inc., Aichi (JP)

( * ) Notice: Subject to any disclaimer, the term of this patent is extended or adjusted under 35 U.S.C. 154(b) by 366 days.

(21) Appl. No.: 10/204,679

(22) PCT Filed: Mar. 29, 2001

(86) PCT No.: PCT/JP01/02656

§ 371 (c)(1),
(2), (4) Date: Aug. 23, 2002

(87) PCT Pub. No.: WO01/73102

PCT Pub. Date: Oct. 4, 2001

(65) Prior Publication Data

US 2003/0194469 A1    Oct. 16, 2003

(30) Foreign Application Priority Data

Mar. 29, 2000  (JP)  ............................. 2000-092133

(51) Int. Cl.
C12P 17/06   (2006.01)
C12P 19/12   (2006.01)
C12N 9/24    (2006.01)

(52) U.S. Cl. ...................... 435/125; 435/100; 435/200
(58) Field of Classification Search ................ 435/200, 435/100, 125

See application file for complete search history.

(56) References Cited

U.S. PATENT DOCUMENTS

| 5,726,034 A | 3/1998 | Bryan et al. |
| 5,789,581 A | 8/1998 | Matsuura et al. |
| 5,827,682 A | 10/1998 | Bryan et al. |

FOREIGN PATENT DOCUMENTS

| JP | 8-140675 | 6/1996 |
| JP | 8-214787 | 8/1996 |
| JP | 11-89589 | 4/1999 |
| WO | WO 95/10512 A1 | 4/1995 |
| WO | WO 95/10530 A1 | 4/1995 |
| WO | WO 00/18931 A1 | 4/2000 |

OTHER PUBLICATIONS

Hoesel et al Development and distribution of isoflavone-O-Beta glycoside specific beta glycosidases in Cicer-arietinum. Planta Medica (1976) vol. 30, No. 2, pp. 97-103.*

W. Hosel et al. "Beta-Glucosidases from Cicer arietinum L.", Eur. J. Biochem. 57:607-616. (1975).*

Hösel, W. Glycosylation and Glycosidases. In "T'he Biochemistry of Plants, a comprehensive treatise. vol. 7, Secondary Plant Products", ed. Conn, E. E., Acadernic Press. New York. pp. 725-753(1981).*

Hay, G. W. et al., "Degradation of rutin by Aspergillus flavuas: Purification and characterization of rutinase". Can. J Microbiol., 7: 921-932 (1961).*

Suzuki H., "Hydrolysis of flavonoid glycosides by enzymes (rhamnodiastase) from Rhamnus and other sources". Arch. Biochem. Biophys., 99: 476-483 (1962).*

V.D. Bokkenheuser et al. "Hydrolysis of Flavonoids by Human Intestinal Bacteria", Progress in Clinical and Biological Research, 280(Plant Flavonoids Biol. Med. 2: Biochem., Cell., Med. Prop.), 143-5, (1988).*

European Search Report.

Hosel, W., "Purification and Properties of 2-Beta Glycosidases from Cicer-Arietinum with Preferential Specificity for Biochanin A 7-Beta Apiosyl Glucoside," Hoppe-Seyler's Z. Physiol. Chem. Bd., vol. 357, No. 12, pp. 1673-1681, Dec. 1976, abstract only.

Gao et al., "A Primeverosidase as a Main Glycosidase Concerned with the Alcoholic Aroma Formation in tea leaves," Biosci. Biotech. Biochem., vol. 59, No. 5, pp. 962-964, 1995.

Gao et al., "Isolation and Characterization of a β-Primeverosidase Concerned with Alcoholic Aroma Formation in Tea Leaves," Biosci. Biotech. Biochem., vol. 60, No. 11, pp. 1810-1814, 1996.

Ogawa, K., et al., "Purification of a β-Primeverosidase Concerned with Alcoholic Aroma Formation in Tea Leaves (Cv. Shuixian) To Be Processed to Oolong Tea," J. Agric. Food Chem., vol. 45, No. 3, pp. 877-882, 1997.

Spielman, L. L., et al: "A Specific Stain for 18-20 α-Glucosidases in Isoelectri Focusing Gels" Analytical Biochemistry, vol. 120, No. 1, 1982 pp. 66-70, XP009000499.

Mach, R. L., et al.: "The bgl1 gene of Trichoderma reesei QM 9414 encodes an extracellular, cellulose-inducible β-glucosidase involved in cellulase induction by sophorose" Molecular Biology, Blackwell Scientific, Oxford, GB, vol. 16, No. 4, May 1995, pp. 687-697, XP001080361.

(Continued)

Primary Examiner—Rebecca Prouty
(74) Attorney, Agent, or Firm—Sughrue Mion, PLLC

(57) ABSTRACT

A physiologically active substance of aglycon type, in particular, aglycon isoflavone, can be efficiently produced, without resort to any acid/alkali treatment or fermentation and substantially without changing the physical properties of a material, by treating the material with a sufficient amount of diglycosidase for a sufficient period of time at an appropriate temperature and pH so that a physiologically active substance of glycoside type contained in the material can be converted into the physiologically active substance of aglycon type. Moreover, by using diglycosidase and/or a specific enzyme preparation, the aglycon content in a protein or protein-containing food can be increased and the flavor thereof can be improved.

6 Claims, 3 Drawing Sheets

OTHER PUBLICATIONS

Kan, V. L. et al.: "β1,4-Oligoglucosides Inhibit the Binding of *Aspergillus fumigatus* Conidia to Human Monocytes" Journal of Infectious Diseases, Chicago, IL, US, vol. 163, No. 5, Jan. 1991, pp. 1154-1156, XP001079462.

Ichigo, H., et al., "Summary of the Studies on the Scent Evolusion During Flower Opening," Fragrance Journal, vol. 27, No. 2, pp. 21-27, Feb. 1999, Abstract only.

Sakata, K., et al., "Beta-Primeverosidase Concerned with the Floral Tea Aroma Formation During Processing of Oolong Tea and Black Tea," Abstracts of Papers American Chemical Society, vol. 217, No. 1-2, pp. 77, 1999.

Ijima Y., et al "Characterization of β-primeverosidase, being concerned with alcoholic aroma formation in tea leaves to be processed into black tea, and preliminary observation on its substrate", J. Agric. Food Chem. (May, 1998), vol. 46, No. 5, pp. 1712-1718.

Hoh Y., et al., "Property of β-glucosidase purified from Aspergillus niger mutants USDB 0827 and USDB 0828", Applied Microbiology Biotechnology (1992), vol. 37, No. 5, pp. 590-593.

Witkowski et al. (1999) Biochemistry 38: pp. 11643-11650.

Branden et al. "Introduction to Protein Structure", Garland Publishing Inc., New York, 1991. p. 247.

Narikawa et al. (2000) Biosci Biotechnol Biochem 64: pp. 1317-1319.

Biochemistry, 2$^{nd}$ Ed., Voet et al., 1995, John Wiley and Sons, Inc., New York, pp. 256-262.

Fundamentals of Organic Chemistry, 3$^{rd}$ Ed., Solomons, 1990, John Wiley and Sons, Inc., New York, p. 862.

America Heritage Dictionary 4$^{th}$ Ed., 2000 (www.bartleby.com/61/9/10070900.html), entry for-in suffix.

McCormack et al., Biotechnol Lett 13(9):677-682 (1991).

International Search Report.

Masaru Matsuura, et al., "B-Glucosidases from Soybeans Hydrolyze Daidzin and Genistin." Journal of Food Science, vol. 58, No. 1, pp. 144-147, 1993.

\* cited by examiner

PROCESS FOR PRODUCING AGLYCON BY USING DIGLYCOSIDASE AND FLAVOR-IMPROVED FOOD CONTAINING THE AGLYCON AND CONVERTING AGENT TO BE USED IN THE PROCESS

TECHNICAL FIELD

The present invention relates to a process for producing an aglycon, a process for producing a protein having an increased aglycon content or a food containing said protein, a process for producing a flavor-improved protein or a food containing said protein, and a process for forming an isoflavone in a living body. The invention may be utilized, for example, for producing processed foods, health foods, dietary supplements, and medicaments.

BACKGROUND ART

Glycosides are chemical substances wherein a saccharide is bonded to a non-saccharide part called aglycon, and are widely present in nature.

Some glycosides are known to exhibit physiological activity through decomposition into aglycons by a glycosidase such as glucosidase produced by enteric bacteria though the glycosides themselves do not exhibit the physiological activity because of their poor enteric absorption, as phytochemicals (phytogenic functional ingredients) such as polyphenols having antioxidation action and phytoestrogens having a weak estrogenic action. Thus, in view of preventing and symptom-alleviating effects of life-style related diseases such as cancer, arteriosclerosis, osteoporosis, and climacteric disorder, and diseases owing to aging, attention has been focused on soybean protein concentrates, soybean-processed materials, and food containing the soybean protein concentrates.

Among the phytochemicals, glucosides that contain isoflavones as aglycons as represented by the following general formula (hereinafter, sometimes referred to as isoflavone glucosides) contain aglycons such as daidzein, genistein, glycitein, and it is revealed from cellular level investigations and epidemiological surveys that they inhibit growth of breast cancer and prostatic cancer cells, alleviate arteriosclerosis and osteoporosis, and also alleviate climacteric disorder owing to the female hormone-like estrogenic action.

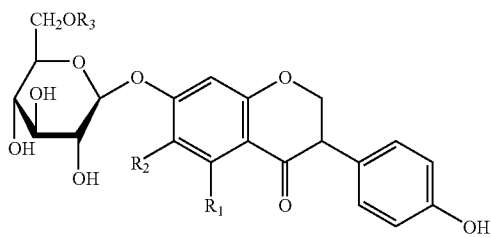

(wherein $R_1$ and $R_2$ each is independently selected from the group consisting of H, OH, and $OCH_3$, and $R_3$ is selected from the group of H, $COCH_3$, $COCH_2COOH$, and $COCH_2CH_2COOH$)

However, there is a possibility that a sufficient amount of glycosidase cannot be produced by enteric bacteria in elderly persons, sick persons, and antibiotics-administered patients, and also a glycosidase is difficult to decompose glycosides modified with acetyl or malonyl group and disaccharide or trisaccharide glycosides, so that it cannot be expected to absorb a sufficient amount of phytochemicals contained in soybean protein concentrates and the like.

Moreover, it is avoided to take foods containing soybean-processed materials such as soybean protein concentrates especially in Western countries owing to the distinctive smell and bitterness, and thus some limitation exists as sources of aglycon isoflavones.

Accordingly, a process for forming phytochemicals efficiently in a living body, and an improvement of flavor of a soybean-processed material rich in aglycon isoflavones, which are highly efficiently absorbed and capable of ingesting a sufficient amount of isoflavones by taking small amount of them, and having less smell and bitterness distinctive of soybean or of a food containing the soybean-processed material have been desired.

On the other hand, the method for converting an isoflavone glucoside into an aglycon isoflavone is known as described in JP-A-10-117792. In this method, a phytogenic protein extract is treated with an alkali to convert a modified glucoside isoflavone into a glucoside isoflavone, which is then subjected to a treatment with glycosidase. Such a treatment is carried out because conventional glycosidase cannot act directly on the modified glucoside isoflavone. Thus, the method is accompanied by the problems of requirement of two steps, enhancement of bitterness by the alkali-treatment, change in physical properties and ingredients, formation of by-products, waste liquid after the alkali-treatment, and the like. Also, glucosidase which takes charge of a main part of the action tends to be influenced by free glucose, so that the kind and concentration of the material used for the production may be limited.

Moreover, JP-A-8-214787 describes a process for converting a glucoside isoflavone into an aglycon isoflavone by fermentation using a microorganism. However, there are possibilities of decomposing the resulting aglycon isoflavone by the microorganism and of forming unexpected by-products, and therefore many problems may arise at the actual production.

Furthermore, a method of hydrolysis with an acid such as hydrochloric acid may be a candidate, but the decomposition of proteins, phospholipids, neutral lipids, and other ingredients may occur along with formation of by-products because of the severe conditions. Especially, the formation of chlorinated compounds such as MCP (monochloropropanol) and DCP (dichloropropanol) whose carcinogenicity has been reported cannot be avoided.

Therefore, an object of the invention is to provide a process for producing a phytogenic physiologically active substance of aglycon type efficiently without resort of any acid/alkali treatment or fermentation and substantially without changing the physical properties of a material. Moreover, other objects of the invention are to enhance the aglycon content in a protein or a protein-containing food by using diglycosidase and/or a specific enzyme preparation and to improve the flavor. These objects and other objects will be further clarified by the following detailed explanations.

DISCLOSURE OF THE INVENTION

As a result of extensive studies, we have found that diglycosidase discovered from origins of various microorganisms efficiently decompose glycosides which are difficult to decompose by conventional glycosidase and also acts even in a living body, and thus accomplished the invention.

Furthermore, we have found that the invention can be conducted using any diglycosidase from any source.

Namely, the invention relates to the following.

(1) A process for producing an aglycon which comprises forming an aglycon by treating, with diglycosidase, a glycoside containing a compound selected from the group consisting of phytoestrogens, polyphenols, isoflavones, biochanin A, formononetin, cumestrol, and lignans as the aglycon.

(2) The process for producing an aglycon according to claim 1, wherein the aglycon is an isoflavone.

(3) The process for producing an aglycon as described above, wherein the glycoside containing an isoflavone as the aglycon is one or more selected from the group consisting of daidzin, genistin, or glycitin and acetyl derivatives, succinyl derivatives, or malonyl derivatives thereof.

(4) The process for producing an aglycon as described above, wherein the diglycosidase is a glucose-tolerant one.

(5) The process for producing an aglycon as described above, wherein the diglycosidase is diglycosidase produced by *Penicillium multicolor* IAM7153.

(6) A process for producing a protein having an increased aglycon content or a food containing the protein, which comprises a step of treating a protein or protein-containing food with diglycosidase.

(7) The process for producing a protein having an increased aglycon content or a food containing the protein as described above, wherein the protein or protein-containing food contains a glycoside containing an isoflavone as the aglycon.

(8) The process for producing a protein having an increased aglycon content or a food containing the protein as described above, wherein the protein or protein-containing food to be produced is a further flavor-improved one.

(9) The process for producing a protein having an increased aglycon content or a food containing the protein as described above, wherein the glycoside containing an isoflavone as the aglycon is one or more selected from the group consisting of daidzin, genistin, or glycitin and acetyl derivatives, succinyl derivatives, or malonyl derivatives thereof.

(10) The process for producing a protein having an increased aglycon content or a food containing the protein as described above, which further comprises a step of treating with an enzyme preparation containing mainly at least one enzyme selected from the group consisting of amylases, proteases, lipases, α-glucosidases, and yeast-dissolving enzymes.

(11) The process for producing a protein having an increased aglycon content or a food containing the protein as described above, wherein the improvement of flavor is reduction of bitterness and/or astringency.

(12) A process for producing a flavor-improved protein or a food containing the protein, which comprises a step of treating with an enzyme preparation containing mainly at least one enzyme selected from the group consisting of amylases, cellulases, pectinases, proteases, lipases, α-glucosidases, α-galactosidase, and yeast-dissolving enzymes.

(13) The process for producing a flavor-improved protein or a food containing the protein as described above, wherein the protein or protein-containing food contains a glycoside containing a flavonoid as the aglycon.

(14) The process for producing a flavor-improved protein or a food containing the protein as described above, wherein the protein or protein-containing food contains a glycoside containing an isoflavone as the aglycon.

(15) A method of administering diglycosidase orally to form an aglycon from a glycoside in a living body.

(16) The method as described above, wherein diglycosidase is orally administered to form an aglycon in a living body from a glycoside containing an isoflavone as the aglycon.

(17) A method of converting a physiologically active substance of glycoside type into a physiologically active substance of aglycon type, which comprises treating the physiologically active substance of glycoside type with diglycosidase.

(18) A process for producing a composition rich in a phytogenic physiologically active substance of aglycon type, which comprises treating a phytogenic material containing a phytogenic physiologically active substance of glycoside type with diglycosidase.

(19) A method of accelerating a bioabsorption of a physiologically active substance, which comprises administering diglycosidase orally before, during, or after the ingestion of a food containing a physiologically active substance of glycoside type.

(20) An agent converting a physiologically active substance of glycoside type into the physiologically active substance of aglycon type, which contains at least diglycosidase.

These embodiments and other embodiments of the invention will be further clarified by the following detailed explanations.

Diglycosidase described in the invention efficiently acts on the glycosides that contain a compound selected from the group consisting of phytoestrogens, polyphenols, isoflavones, biochanin A, formononetin, cumestrol, and lignans as the aglycon (hereinafter, also referred to as aglycon glycoside), can very efficiently act especially on the glycosides containing an isoflavone as the aglycon (hereinafter, also referred to as isoflavone glycosides), and is hardly influenced by free glucose. Therefore, the process can be advantageously carried out in the case that the isoflavone glycoside is daidzin, genistin, or glycitin, or an acetyl derivative, succinyl derivative, or malonyl derivative thereof. By the way, the isoflavone formed from the isoflavone glycoside is also referred to as aglycon isoflavone.

Moreover, by administering the diglycosidase, the preventive effect on various diseases can be enhanced through the formation of an isoflavone from an aglycon glycoside or a food containing the same which is orally ingested. Diglycosidase produced by *Penicillium multicolor* IAM7153 is preferably used as diglycosidase. β-Galactosidase derived from *Penicillium multicolor* is an enzyme which is described in Food Additives List and whose safety is recognized, and thus diglycosidase produced by such highly safety bacterium is estimated to be highly safe.

Furthermore, in the case of using soybean as a starting material, although the benefit of soybean protein concentrates and soybean-processed materials to health is reported, ingestion of them are avoided especially in Western countries owing to the distinctive smell and bitterness. The above-mentioned acetylglycoside isoflavones and malonylglycoside isoflavones have a strong bitterness but the aglycon isoflavones have less bitterness. Therefore, a food wherein bitterness of soybean protein concentrate or soybean-processed material is efficiently reduced can be provided by the conversion into aglycon isoflavones by diglycosidase.

When such soybean protein concentrate or soybean-processed material wherein isoflavones are concentrated as aglycons having higher absorption efficiency is used, a sufficient amount of isoflavones can be ingested through a little intake, and also the form can be changed to a form easily ingested by people who avoid the smell and strange taste distinctive of soybean.

Moreover, owing to the smell and strange taste of soybean protein concentrates or soybean-processed materials, the amount used is limited in the case of using them as food materials, and therefore soybean protein concentrates or soybean-processed materials have a limitation as isoflavone sources for foods. According to the invention, use of the soybean protein concentrates or soybean-processed materials, wherein isoflavone glycosides are digested with diglycosidase and concentrated as isoflavone aglycons which have higher absorption efficiency and less bitterness, enables supply of isoflavones to foods through a little use of the concentrates or materials, so that they can be utilized for many kinds of foods as isoflavone sources.

Diglycosidase for use in the invention is characterized in that it has an activity of acting on a disaccharide glycoside, which is difficult to utilize as a substrate by conventional glucosidase, to isolate a saccharide as a two-saccharide unit from the disaccharide glycoside and also to form an aglycon. Herein, an enzyme having the above activity is referred to as "diglycosidase".

The diglycosidase in the invention is an enzyme which is classified into a saccharide-chain hydrolase but has a property different from the properties of conventional α- and β-glycosidases. Diglycosidase can utilize, as a substrate, so-called a glycoside wherein a linear or branched saccharide chain composed of single or two or more kinds of saccharides is bonded to a compound other than a saccharide through hydroxyl group in the saccharide chain, and recognizes the substrate at the two-saccharide unit to cleavage it, whereby corresponding disaccharide and an aglycon having a saccharide chain with two saccharide-smaller chain length are formed successively and finally, an aglycon is formed. Additionally, it also decomposes modified glucosides such as acetyl derivatives, succinyl derivatives, and malonyl derivatives, which are difficult to decompose by conventional glucosidase, into saccharides and aglycons. As representative examples of saccharides present in nature, starch, cellulose, polysaccharides constituting cell walls, and the like may be mentioned. Many kinds of saccharide chains may be suitable for the saccharide chains of glycosides, and examples thereof include 6-O-β-D-xylopyranosyl-β-D-glucopyranoside (β-primeveroside), 6-O-α-L-arabinopyranosyl-β-D-glucopyranoside (vicianoside), 6-O-α-L-arabinofuranosyl-β-D-glucopyranoside, 6-O-α-L-rhamnopyranosyl-β-D-glucopyranoside (rutinoside), 6-O-β-D-apiofuranosyl-β-D-glucopyranoside, 6-O-β-D-glucopyranosyl-β-D-glucopyranoside (gentiobioside), 4-O-α-glucopyranosyl-β-D-glucopyranoside (maltose), 2-O-α-L-rhamnopyranosyl-β-D-galactopyranoside (rhaminose), 6-O-α-L-rhamnopyranosyl-β-D-galactopyranoside (robinobioside), 2-O-β-D-xylopyranosyl-β-D-glucopyranoside (xylosylglucose), 4-O-β-D-glucopyranosyl-β-D-glucopyranoside (cellobioside), xylobioside, and the like. Other than the above-mentioned compounds, any combination of saccharides can be recognized as a substrate for the reaction as far as the combination has a disaccharide structure. Aglycon means a compound to be obtained from a glycoside by eliminating a saccharide of the glycoside. Aglycons of glycosides are widely present in nature, and examples thereof include volatile compounds in plants such as linalool, geraniol, citronellal, phenethyl alcohol, citronellol, jasmones, limonene, terpinene, citral, nerol, pinene, borneol, terpineol, methyl jasmonate, hexanol, hexenol, hexanal, hexenal, vanillin, benzaldehyde, eugenol, methyl salicylate, linalool oxide, benzyl alcohol, and vomifomitol; pigments in plants such as alizarin, purpurin, anthocyanidin including pellagonidin, cyanidin, delphinidin, peonidin, petunidin, and malvidin; and flavonoids such as nariltin, naringenin, hesperetin, neohesperetin, diosmetin, quercetin, campherol, myricetin, isorhamnetin, and syringenin; and the like. Other than the compounds mentioned herein, various compounds may be present as aglycons of glycosides or may become aglycons of glycosides.

Furthermore, diglycosidase can utilize so-called monosaccharide glycosides, wherein one molecule of saccharide is bonded to an aglycon, as substrates to form corresponding monosaccharides and aglycons, other than above-mentioned disaccharide-isolating activity. In particular, it is a characteristic that diglycosidase can act on monosaccharide glycosides which is resistant to hydrolysis by conventional β-glucosidase.

Diglycosidase for use in the invention can be obtained from microorganisms having ability of producing diglycosidase without requiring undue experimental burden from those skilled in the art (For example, cf. WO00/18931).

The microorganisms producing diglycosidase of the invention can be obtained by the following screening, for example. That is, an enrichment culture is carried out by inoculating a soil suspension to a liquid medium for separation containing eugenyl primeveroside or the like as sole carbon source, applying the culture liquid onto a similar plating agar medium for separation and selecting colonies grown. These strains are cultured in a suitable liquid medium and strains having pNP-isolating activity can be selected through cleavage of disaccharide from pNP-primeveroside or the like.

On these strains thus selected, microorganisms producing diglycosidase can be screened using pNP-primeveroside or the like as a substrate and disaccharide isolation as a measure.

The producing ability has been already confirmed on *Aspergillus niger* IFO4407 (available from Institute of Fermentation, 2-17-85, Juso-honmachi, Yodogawa-ku, Osaka), *Aspergillus niger* IAM 2020, *Aspergillus fumigatus* IAM2046, *Penicillium multicolor* IAM7153 (available from Institute of Molecular Cell Biology, the University of Tokyo, 1-1-1, Yayoi, Bunkyo-ku, Tokyo), and the like.

Additionally, in other various microorganisms, the diglycosidase activity has been confirmed on various microorganisms such as the genus *Aspergillus*, the genus *Penicillium*, the genus *Rhizopus*, the genus *Rhizomucor*, the genus *Talaromyces*, the genus *Mortierella*, the genus *Cryptococcus*, the genus *Microbacterium*, the genus *Corynebacterium*, the genus *Actinoplanes*, and the like.

Any strain can be used in the invention as far as it has an ability of producing diglycosidase, and the strain is not limited to the above-mentioned strains. Furthermore, the process for producing diglycosidase usable in the invention includes mutant strains of the strains having a diglycosidase-producing ability, or various microorganisms or various cells (e.g., yeast cells, bacterial cells, higher plant cells, and animal cells) modified so as to be capable of producing diglycosidase by recombinant DNA method, and particularly preferred are those modified so as to be capable of producing diglycosidase with high productivity. In the case that a diglycosidase-producing ability is imparted by introducing a diglycosidase gene, the microorganism used as a host may not have a diglycosidase-producing ability.

For producing diglycosidase using the above various microorganisms, a method and conditions suitable for the culture of the microorganism can be set, and the method and conditions are not particularly limited. For example, any of liquid culture and solid culture may be used for culturing the above various strains, but liquid culture is preferably used. The liquid culture may be carried out as follows, for example.

The medium to be employed may be any medium as far as the microorganism producing diglycosidase is capable of growing in the medium. For example, there may be used media to which carbon sources such as glucose, sucrose, gentiobiose, soluble starch, glycerol, dextrin, molasses, and organic acids; further nitrogen sources such as ammonium sulfate, ammonium carbonate, ammonium phosphonate, ammonium acetate, or peptone, yeast extract, corn steep liquor, casein hydrolysate, bran, and meat extract; and further inorganic salts such as potassium salts, magnesium salts, sodium salts, phosphonates, manganese salts, iron salts, and zinc salts are added. Furthermore, for accumulating diglycosidase, various inducing substances may be added to the medium. As the inducing substances, saccharides may be used, for example, and there may be preferably used gentose (e.g., gentose #80, Nihon Shokuhin Kako Co., Ltd.), gentiobiose, genti-oligosaccharide (e.g., gentiologo etc., Wako Pure Chemical Industries, Ltd.), galactomannan, and the like. The adding amount of these inducing substances is not particularly limited as far as the productivity of aimed diglycosidase is enhanced, but the substance is preferably added in an amount of 0.01 to 10%.

The pH of the medium is adjusted to from about 3 to 8, preferably from about 5 to 6, and culture is carried out at a temperature of about 10 to 50° C., preferably about 25 to 30° C. for 1 to 15 days, preferably 4 to 7 days under aerobic conditions. As the culturing method, a shaking culture or an aerobic submerged culture by means of a jar fermenter may be utilized. However, the above various culturing conditions may be optionally changed, of course, depending on the microorganism or cell to be cultured, and the conditions are not particularly limited as far as diglycosidase of the invention is produced.

For isolation and purification of diglycosidase from the culture liquid obtained, using a diglycosidase activity as a measure, purified diglycosidase can be obtained by combining centrifugal separation, UF concentration, salting out, and various chromatography such as ion exchange resins, and treating in a usual manner (Referential document: Tanpakusitsu·Kouso no Kisojikkenhou (Basic experimental methods for proteins and enzymes), written by Takekazu Horio, Nankodo).

A culture liquid obtained by culturing the above microorganism may be utilized as such as the enzyme composition of the invention. Of course, the culture liquid may be optionally changed in the degree of purification according to the purpose used in the invention.

The invention provides a process for producing an aglycon which comprises forming an aglycon by treating, with diglycosidase, a glycoside containing a compound selected from the group consisting of phytoestrogens, polyphenols, isoflavones, biochanin A, formononetin, cumestrol, and lignans as the aglycon. The producing process includes the reaction of a phytogenic material containing the above compound as the aglycon with a sufficient amount of diglycosidase under weakly acidic conditions at an appropriate temperature and pH for a sufficient period of time so as to convert at least most of the glycoside in the starting material into an aglycon, whereby an aglycon is produced. The invention provides a producing process wherein diglycosidase is added to a plant extract in order to produce a plant extract rich in an aglycon.

The novel process is a one-step process of converting most of an aglycon glycoside into free aglycon by an enzyme preparation containing a hydrolase of disaccharide glycosides, i.e., diglycosidase. The process is effective for the aglycon glycosides present in phytogenic materials, preferably proteins or protein foods. Since the process is found to be capable of substantially complete conversion of modified glucoside isoflavones and glucoside isoflavones into aglycon isoflavones, it includes the conversion of modified glucoside isoflavones and glucoside isoflavones into aglycon isoflavones. In some phytogenic protein materials, particularly soybean protein materials, substantial part of total isoflavone contents in the phytogenic protein materials is present in the form of isoflavone glycosides. Therefore, not only the conversion of glycoside isoflavones into aglycon isoflavones but also the conversion of modified glycoside isoflavones into aglycon isoflavones are necessary for maximum increase of the amount of aglycon isoflavones obtainable from the phytogenic protein materials.

The starting material in a preferred embodiment is any protein or protein-containing food (more preferably a phytogenic material, phytogenic protein, or phytogenic protein-containing food) containing a physiologically active substance of glycoside type. Some processes in the following explanations are described using soybean products as examples, but the process of the invention can be generally applied to a wide range of proteins or protein-containing foods other than soybean and soybean products.

In the invention, the "protein or protein-containing food" preferably contains a physiologically active substance of glycoside type but is not particularly limited.

The "phytogenic material" in the invention means a whole plant body which is edible or used as a medicine, or a part thereof such as leaf, flower, fruit, stem, or root, or a processed product thereof. Examples thereof include whole plant bodies harvested, or parts thereof such as leaf, flower, fruit, stem, and root, and plant extracts and processed products thereof. Specific examples of the phytogenic material include the following materials: phytogenic proteins such as soybean protein, soymilk, juices (orange juice, grape juice, apple juice, pomegranate juice), herb tea, plant extracts such as herb extract, and processed products of the above materials such as juice drinks, wine, tea, black tea, and cocoa.

The "phytogenic protein" means a protein obtainable from the above "phytogenic material", and may be a mixture with other ingredients derived from the phytogenic material.

In the invention, the "compound selected from the group consisting of phytochemicals, phytoestrogens, polyphenols, isoflavone, biochanin A, formononetin, cumestrol, and lignans" is not particularly limited as far as the compound falls within these conceptual range, but it is preferably a compound which exhibits a physiological activity or enhances a physiological activity in a living body (preferably a warm-blooded animal, more preferably human). The compound is preferably a flavonoid, more preferably an isoflavone, most preferably an isoflavone represented by the above structural formula.

The "physiologically active substance" in the invention means a substance, most of which is preferably present as a glycoside in a plant body and which exhibits a physiological activity or enhances a physiological activity in a living body upon the conversion into the aglycon type. Specifically, the physiologically active substance includes phytochemicals, phytoestrogens, polyphenols, isoflavone, biochanin A, formononetin, cumestrol, and lignans as mentioned above, and preferred are isoflavones.

The "physiologically active substance of glycoside type" means that the aglycon of the above glycoside is a physiologically active substance, and the saccharide chain is composed of one or more saccharide, preferably two or more saccharides. The two-saccharide chains include those mentioned above and the like.

The "enzyme preparation containing mainly at least one enzyme selected from the group consisting of amylases, proteases, lipases, α-glucosidases, and yeast-dissolving enzymes" is not particularly limited as far as it mainly contains these enzymes, and commercially available enzymes may be employed. The following will illustrates those manufactured by Amano Enzyme Inc. Examples of amylase include Amylase AD "Amano" 1 (optimum pH: 6.0, optimum temperature: 70° C.), Gluczyme NL 4.2 (optimum pH: 4.5, optimum temperature: 65° C.), Transglucosidase L "Amano" (optimum pH: 5.0, optimum temperature: 60° C.), and the like. Examples of cellulase include Cellulase A "Amano" 3 (optimum pH: 4.5, optimum temperature: 55° C.), Cellulase T "Amano" 4, Hemicellulase "Amano" 90G (optimum pH: 4.5, optimum temperature: 50° C.), Hemicellulase GM "Amano", and the like. Examples of pectinase include Pectinase PL "Amano" (optimum pH: 4.55–0, optimum temperature: 60–55° C.) and the like. Examples of protease include Umamizyme, Newlase F3G, Papain W-40, Pancreatin F, Protease B, Protease A "Amano" G. and the like, and examples of lipase include Lipase A "Amano" 6 (optimum pH: 6.5, optimum temperature: 45° C.), and the like. A yeast-dissolving enzyme preparation YL-15 (optimum pH: 7.0, optimum temperature: 50–55° C.) is mentioned as a yeast-dissolving enzyme, and ADG-S-DS (optimum pH: 4.5–5, optimum temperature: 50–60° C.) and the like are mentioned as an α-galactosidase.

The above enzymes and enzyme preparations can be produced by known methods. For example, an enzyme can be obtained by screening a microorganism producing a specific enzyme mentioned above in a similar manner to the production of diglycosidase and culturing the resulting enzyme-producing strain in a suitable medium. Examples of the above enzyme-producing strain include *Bacillus subtillis, Aspergillus niger, Aspergillus oxyzae, Trichoderma viride, Rhizopus nivenus, Pseudomonas* sp., and the like.

The following will explain the invention in further detail with regard to the process for producing a protein having an increased aglycon content or a food containing the protein, which comprises a step of treating a protein or protein-containing food with diglycosidase, by way of illustration of a phytogenic physiologically active ingredient (especially an isoflavone glycoside) derived from a phytogenic material, but the invention can be conducted using any above compound other than the phytogenic physiologically active ingredient derived from a phytogenic material. By the way, the term of soybean material used herein means any type of soybean or variants of soybeans.

Some different embodiments are possible as specific processes for carrying out the invention.

In the first embodiment, a phytogenic physiologically active substance of glycoside type is converted into a phytogenic physiologically active substance of aglycon type while the phytogenic physiologically active substance is left in the phytogenic material. Therefore, the formed phytogenic physiologically active substance of aglycon type may be left in the phytogenic material or may be suitably removed. The aglycon form of the phytogenic physiologically active substance may be generally removed by a solvent, hydrophobic effluence or extraction. The solvent suitable for the operation includes acetone, ethanol, and other similar organic solvents, but is not limited thereto.

In the second embodiment, a phytogenic physiologically active substance of glycoside type (e.g., isoflavone modified glycoside or isoflavone glucoside) in a phytogenic material is removed from the phytogenic material by aqueous effluence or extraction. The aqueous effluence is carried out through the effluence of relatively soluble phytogenic physiologically active substance of glycoside type by immersing the phytogenic material or by exposing the phytogenic material to or dipping it in water or a mixture of hydrophilic solvents such as ethanol or other alcohols. The pH of the resulting aqueous solution is from about pH 2 to about pH 5, preferably about pH 4. After removal, the phytogenic physiologically active substance of glycoside type is converted into the phytogenic physiologically active substance of aglycon type.

In the third embodiment, prior to all the operations for conversion, a phytogenic physiologically active substance of glycoside type is removed from a phytogenic material.

Depending on the type of phytogenic material containing a phytogenic physiologically active substance of glycoside type, in some cases, the phytogenic material is preferably processed to a finely crushed form. This operation is desirable for bringing a phytogenic physiologically active substance in the phytogenic material into contact with a reagent (diglycosidase) employed in the step which will be described in detail in the following. The material may be subjected to grinding, crushing, or other processing. When the phytogenic material is in condition that isoflavone compounds in the phytogenic material easily come into contact with an external reagent or reactant, e.g., a small leaf part in a plant, it is not necessary to subject the phytogenic material to the above processing.

The conversion of a phytogenic physiologically active substance of glycoside type into the phytogenic physiologically active substance of aglycon type is sometimes partially carried out by enzymes present in the mixture depending on the phytogenic material used. These enzymes may be present naturally in phytogenic protein materials or may be derived from microorganisms grown in the materials. Such enzymes are called as residual enzymes. However, there is a possibility that the conversion of the phytogenic physiologically active substance of glycoside type into the phytogenic physiologically active substance of aglycon type cannot be carried out sufficiently depending on the nature and concentration of the residual enzyme in the phytogenic protein materials. By adding an enzyme preparation containing an external enzyme, i.e., diglycosidase, maximum converting efficiency of the phytogenic physiologically active substance of aglycon type can be achieved.

In the invention, the amount of the enzyme to be added depends on various factors including the type of enzyme present, the distribution of enzyme concentration, the pH of reaction system, the activity of enzyme present, and temperature. In the case of adding an enzyme, typically preferred enzyme amount is preferably from 28 to 2800 AU, usually from 10 to 10000 AU relative to 100 g of a phytogenic material as total concentration of enzyme present based on dry weight thereof. When a sufficient concentration of enzymes including a residual enzyme, an additional enzyme or both enzymes are present in the system, a phytogenic physiologically active substance of glycoside type is brought into contact with the enzymes at an appropriate temperature and pH for a sufficient period of time so as to convert substantially all the phytogenic physiologically active substance of glycoside type in the mixture into the phytogenic physiologically active substance of aglycon type.

The conversion-production step is preferably carried out at a pH of about 2 to about 6. More preferred pH range for the conversion-production step is from about 3 to about 5. Depending on the phytogenic material used, the pH may be adjusted with an acidic reagent such as hydrochloric acid, phosphoric acid, acetic acid, or sulfuric acid, or an alkaline reagent such as sodium hydroxide. In many cases, it is assumed to use an acidic or alkaline reagent of food grade. The temperature to be used in the conversion-production step is preferably from about 25° C. to about 65° C. More preferred temperature is from about 30° C. to about 55° C. Throughout the reaction, the temperature is usually constant, but the temperature may be elevated or lowered according to the successive step and final intended use. Namely, it may be relatively freely changed according to the various circumstances of the situation.

The period of time necessary for the conversion and production may be determined depending on complicated relationship between various factors of the kind, concentration, and physical properties of the material to be reacted, the concentration of the enzyme added, and further the temperature and pH of the reaction system. In most cases, the conversion-production can be substantially completely achieved within 6 to 12 hours. The period of time for the conversion-production can be shortened depending on the concentration of the diglycosidase preparation added. At the conversion-production step, most of the isoflavone glycoside in the mixture can be converted into the aglycon isoflavone. The efficiency of the conversion is usually at least about 50% or more, preferably about 70% or more. By adopting the above preferable reaction conditions, nearly complete conversion can be achieved.

By adopting conditions similar to the above, it is possible to carry out a process of the invention for producing an aglycon which comprises forming an aglycon by treating, with diglycosidase, a glycoside containing a compound selected from the group consisting of phytoestrogens, polyphenols, isoflavones, biochanin A, formononetin, cumestrol, and lignans as the aglycon.

In addition to the above step, in the invention, the process may further comprise a step of treating with an enzyme preparation containing mainly at least one enzyme selected from the group consisting of amylases, proteases, lipases, α-glucosidase, and yeast-dissolving enzymes. This step may be conducted before or after the step of treating with diglycosidase, or the treatment with diglycosidase and the enzyme preparation may be carried out at the same time. In this case, the treatment with diglycosidase and the enzyme preparation at the same time is carried out under the conditions similar to those in the case of using diglycosidase solely. Moreover, when the treatment with an enzyme preparation is carried out before or after the treatment with diglycosidase, the pH, temperature, period of time, and the like may be selected in consideration of optimum pH and optimum temperature of the above each enzyme preparation. This process is also accompanied by the effects of increasing aglycon content in a protein or protein-containing food and of improving flavor through the reduction of bitterness and/or astringency.

Additionally, in the invention, during the process of finding the above effects of the combined use with diglycosidase, it was found that flavor is improved by treating a protein or protein-containing food with a specific enzyme preparation alone, i.e., an enzyme preparation containing mainly at least one enzyme selected from the group consisting of amylases, cellulases, pectinases, proteases, lipases, α-glucosidase, α-galactosidases, and yeast-dissolving enzymes. With regard to the treating conditions in this case, the pH is preferably from 3 to 8, more preferably from 5 to 7.5, and the treating temperature and treating time are similar to the case of the combined use with diglycosidase. By the way, the treated product may be optionally adjusted to a desired pH.

By treating a protein or protein-containing food as mentioned above, the flavor of the protein or protein-containing food can be improved and particularly, bitterness and/or astringency can be reduced.

In addition, by administering the phytogenic physiologically active substance of aglycon type produced as above or a composition rich in the phytogenic physiologically active substance of aglycon type as such or as a mixture with a food or drink, the effect derived from the phytogenic physiologically active substance can be attained. The effects of the phytogenic physiologically active substance include effects of preventing various diseases (cancer, life-style related diseases, osteoporosis, a burning sensation in climacteric disorder, and the like), and of regulation of intestinal function, immunostimulation, and biophylactic action. Moreover, other than the administration of the phytogenic physiologically active substance which is converted into aglycon type beforehand, by administering orally a phytogenic physiologically active substance of glycoside type and/or a phytogenic material containing a phytogenic physiologically active substance of glycoside type together with diglycosidase, the phytogenic physiologically active substance of glycoside type is converted into the phytogenic physiologically active substance of aglycon type in a living body, for example in stomach or intestines and the absorption of the phytogenic physiologically active substance of aglycon type and the migration into blood are accelerated, whereby preventive effect of the phytogenic physiologically active substance to various diseases can be enhanced.

The method of accelerating a bioabsorption of a physiologically active substance according to the invention, which comprises administering diglycosidase orally before, during, and/or after the ingestion of a food containing physiologically active substances of glycoside type, (preferably, a method of forming an isoflavone from a glycoside containing an isoflavone as the aglycon in a living body), is conducted as follows.

The target is a warm-blooded animal, preferably human or livestock.

As far as the phytogenic physiologically active substance of glycoside type comes into contact with diglycosidase in stomach and intestines, diglycosidase may be administered at any time before, during, or after the ingestion of a food containing physiologically active substances of glycoside type. Preferred is between just after a meal and one hour after the meal.

The dose of diglycosidase is not particularly limited as far as the conversion of the phytogenic physiologically active substance of glycoside type into the phytogenic physiologically active substance of aglycon type occurs in a living body, but diglycosidase is orally administered in an amount of usually from 10 mg/day to 500 mg/day, preferably from 30 mg/day to 300 mg/day, more preferably 100 mg/day to 200 mg/day. The number of dose is not particularly limited but is preferably from once per several days to several times per day, particularly preferably three times per day (i.e., after every meal).

Moreover, the ingesting amount of the physiologically active substance is not particularly limited as far as its effect is attained, but the substance is ingested in an amount of preferably 10 mg/day or more, more preferably 50 mg/day or more, further preferably 50 mg/day to 100 mg/day.

Furthermore, diglycosidase may be administered solely, as an enzyme preparation, and/or as a mixture with conventional glycosidase (e.g., glucosidase, galactosidase, etc.).

Diglycosidase may be used as an enzyme preparation. In this case, the enzyme preparation contains diglycosidase as the essential ingredient, and may further contain various enzymes, stabilizers, and the like.

Additionally, in the case of the administration as an enzyme preparation mixed with conventional glycosidase, examples of the conventional glycosidase include glucosidase, galactosidase, xylosidase, and rhamnosidase, and the dose of diglycosidase is preferably from 10 mg/day to 50 mg/day.

BEST MODE FOR CARRYING OUT THE INVENTION

Figure 1:
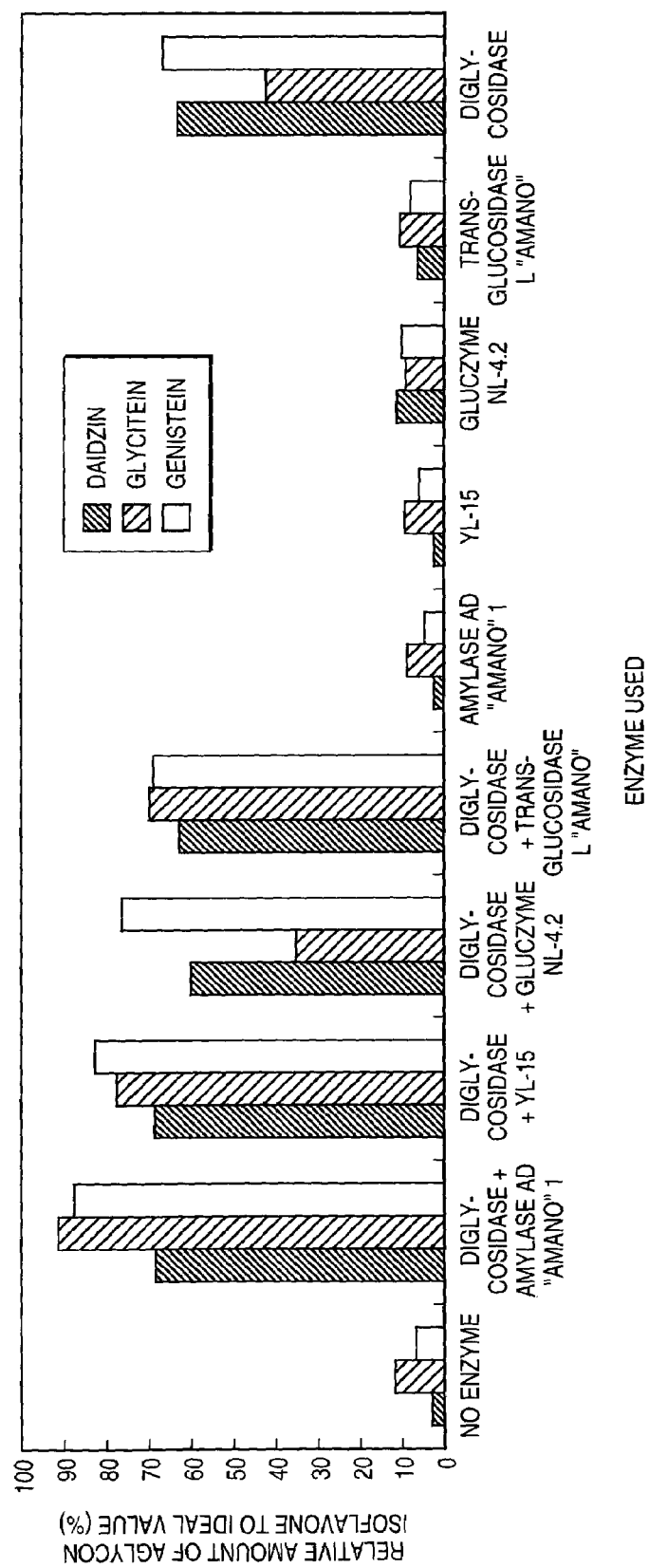
FIG. 1 is a graph showing the results of Example 7.

The invention will be explained in detail with illustrating Examples using soybean materials as phytogenic materials. Examples are illustrated for the purpose of explanation only and they by no means restrict the scope of the invention.

The phytogenic materials, for example defatted soybean, soymilk, concentrated soybean protein, and various soybean products contain 12 kinds of isoflavone compounds. Specifically, they contain aglycons of glycitein, daidzein, and genistein; glucoside glycosides of glycitin, daidzin, and genistin; acetylglycitin, acetyldaidzin, and acetylgenistin having O-acetyl group at 6-position of the glucose residue; and malonylglycitin, malonyldaidzin, and malonylgenistin having O-malonyl group at 6-position of the glucose residue. The existing ratio of these compounds is characteristic to each of the difference of varieties of soybean and the difference of treatment in the production steps.

Unless otherwise stated, ratio, part(s), percent, and the like are herein based on weight.

By the way, the measured activities of various enzymes herein are shown as values obtainable by the method described below unless otherwise stated.

Diglycosidase Activity

The activity was measured on an automatic chemical analyzing apparatus (TBA-30R manufactured by Toshiba Corporation). Thirty μL of an enzyme sample was mixed with 200 μL of 2 mM solution of p-nitrophenyl (pNP) primeveroside used as a substrate of disaccharide glycoside, which is obtained by dissolving the compound in an acetate buffer (pH 5.5), followed by reaction at 40° C. for 9.75 minutes at the cycle time of 22.5 seconds. Then, 250 μL of sodium carbonate was added thereto and then absorbance at 412 nm was measured. A blank derived from the sample was measured similarly using 20 mM acetate buffer (pH 5.5) instead of the substrate solution.

The enzyme amount increasing the absorbance by 1 under the conditions is defined as 1 AU.

The pNP-primeveroside used herein can be synthesized, for example, by reacting pNP-glucoside (manufactured by Merck) with xylo-origosaccharide (manufactured by Wako Pure Chemical Industries, Ltd.) using an enzyme, xylosidase (manufactured by Sigma) to bond xylose to pNP-glucoside in β-1,6-manner via one residue transfer.

EXAMPLE 1

Production of Diglycosidase by *Penicillium multicolor* IAM7153

Culture of Diglycosidase

A medium for growth (pH 5.6) containing 2.0% of defatted soybean, 3.0% of glucose, 0.5% of potassium dihydrogen phosphate, 0.4% of ammonium sulfate, 0.3% of dry yeast was sterilized at 121° C. for 20 minutes. To 100 mL of the sterilized medium was inoculated 1 oese of *Penicillium multicolor* IAM7153, followed by pre-culture at 27° C. at the shaking rate of 140 min$^{-1}$. After 5 days, 20 L of a main medium of pH 4.9 containing 1.0% of Sunfiber R, 2.0% of potassium dihydrogen phosphate, 1.0% of ammonium sulfate, and 3.13% of meast P1G was sterilized in a 30 L jar fermenter at 121° C. for 20 minutes while stirring at 150 min$^{-1}$. The pre-medium was inoculated at a rate of 1.5% and the whole was cultured at a stirring number of 250 min$^{-1}$, an aeration of 0.75 vvm (15 L/min), an inner pressure of 0.5 kg/cm$^2$ (48 kPa), and a temperature of 27±1° C. for 8 days.

Purification of Diglycosidase

To the culture broth were added 2% by weight each, based on total liquid amount, of Zemlite Super 56M and Fineflow A as filtration aids and filtration through diatomaceous earth was carried out. The filtrate was concentrated by a factor of 20 using an ultrafiltration membrane UF AIP-2020 (MW 6,000) and also the substitution by 20 mM acetate buffer of pH 4.7 was conducted. Ammonium sulfate was added to the above ultrafiltration concentrate to conduct 50% ammonium sulfate-salting out. The resulting precipitate was removed and ammonium sulfate was further added to the supernatant to conduct 80% ammonium sulfate-salting out. The precipitate was recovered and dissolved in 20 mM acetate buffer of pH 4.7. The solution was passed through a 10-DG column (BioRad Co.) to exchange the buffer for 20 mM acetate buffer of pH 4.7 containing 30% saturated ammonium sulfate (this solution is also referred to as "crude diglycosidase"). This solution was applied to a hydrophobic chromatography (HiLoad 16/10 Phenyl Sepharose High Performance (Pharmacia)) to separate a fraction showing diglycosidase activity from fractions showing β-glucosidase and β-xylosidase activities. Elution was started at room temperature with 20 mM acetate buffer containing 30% saturated ammonium sulfate at a flow rate of 2 mL/min and elution was carried out by linear gradient of 30 to 0%. A fraction showing diglycosidase activity was eluted at 10 to 12.5% saturated ammonium sulfate concentration. The diglycosidase fraction recovered was concentrated and a centrifuged supernatant was charged onto 10-DG column to exchange the solution for 25 mM tris-hydrochloride buffer of pH 7.1. This liquid was applied to an isoelectric chromatography (Mono-P HR5/20 (Pharmacia)) and elution was started at room temperature with polybuffer 74 of pH 5.0 at 1 mL/min. The aimed diglycosidase activity was eluted from pH 6.2 to pH 6.3. Since a single band was obtained on an SDS electrophoresis of the fraction, it was proved that diglycosidase (hereinafter, also referred to as "purified diglycosidase") could be purified.

EXAMPLE 2

Reactivity of Diglycosidase Toward Various Isoflavone Glycosides

Diglycosidase was diluted with an acetate buffer of pH 4.0 to prepare a 0.75 AU/mL enzyme solution. As references, a similar operation was conducted using β-glucosidase (manufactured by Fluka) derived from *Aspergillus niger*, β-glucosidase (manufactured by Sigma) derived from almond, β-xylosidase derived from pectinase G (manufactured by Amano Enzyme Inc.). Each of purified products of isoflavone glycosides (glycitin, acetylglycitin, malonylglycitin, daidzin, acetyldaidzin, malonyldaidzin, genistin, acetylgenistin, malonylgenistin, all manufactured by Nacalai Tesque, Inc.) was dissolved in methanol to prepare each 2 mM substrate solution. The reaction was carried out by mixing 10 μL of a substrate solution, 200 μL of 20 mM acetate buffer (pH 4.0), and 40 μL of each purified enzyme solution at a total liquid volume of 250 μL. The reaction was carried out at 55° C. and isolation of an aglycon isoflavone from an isoflavone glycoside in the reaction mixture was detected by HLPC at 0, 1, 3, and 6 hours of the reaction.

HLPC Analysis

To the reaction mixture was added 700 μL of ethanol, followed by stirring and ultrasonication. After centrifugation at 15,000 rpm and 4° C. for 10 minutes, the supernatant was filtered through a filter and then the filtrate was applied to HPLC.

The isoflavone glycoside and aglycon isoflavone contained in the filtrate was separated and detected by a high performance liquid chromatography (HPLC, Shimadzu CLASS LC-10 system) using TOSOH TSK gel ODS-80TM column (manufactured by Tosoh Corporation). The filtrate containing an isoflavone glycoside and an aglycon isoflavone was injected into the column by means of an auto-injector (Shimadzu, SIL-10AXL) and elution was started with a solution containing 2% of eluting solution A (acetonitrile) and 98% of eluting solution B (10% acetic acid solution), and after 5 minutes, continued by a linear concentration gradient finishing with a solution of 50% of eluting solution A and 50% of eluting solution B. Total flow rate was 0.8 mL/min and 12 kinds of isoflavone glycosides and aglycon isoflavones, i.e., glycitin, daidzin, genistin, 6″-O-acetylglycitin, 6″-O-acetyldaidzin, 6″-O-acetylgenistin, 6″-O-malonylglycitin, 6″-O-malonyldaidzin, 6″-O-malonylgenistin, glycitein, daidzein, and genistein can be separated. The absorbance at 260 nm was detected by a UV detector (Shimadzu, SPD-10AV). Using purified products (manufactured by Nacalai Tesque, Inc.) of the above isoflavone glycosides and aglycon isoflavones, the isoflavone glycoside and aglycon isoflavone were quantitatively determined according to a calibration curve method. By the way, unless otherwise stated, the measuring conditions of HPLC herein mean those described in the example.

As a result, β-glucosidase derived from *Aspergillus niger* could act well on 3 types of glucoside isoflavones of glycitin, daidzin, and genistin, but the reactivity on modified glycosides was very low. β-Glucosidase derived from a plant exhibits a low efficiency of decomposing glycoside isoflavones and no action was observed on modified isoflavones. On the other hand, diglycosidase could cleave all the isoflavone glycosides at a high efficiency. Of these, a high efficiency was observed toward acetylglucoside isoflavones. From the above results, diglycosidase was found to isolate aglycon isoflavones from isoflavone glycosides through cleavage very efficiently (Table 1).

In addition, it was found that the efficiency of decomposing isoflavone glucosides, especially genistin could be further enhanced by the combined use of β-glucosidase in addition to the enzyme.

TABLE 1

| | | Reaction time (h) | | | | | | | |
|---|---|---|---|---|---|---|---|---|---|
| | | 0 | | 1 | | 3 | | 6 | |
| Purified enzyme | Substrate | glucoside | aglycon | glucoside | aglycon | glucoside | aglycon | glucoside | aglycon |
| Diglycosidase derived from P. multicolor | glycitin | 100 | 0 | 2.1 | 97.9 | 0.2 | 99.8 | 0.3 | 99.7 |
| | daidzin | 99.1 | 0.9 | 29.9 | 70.1 | 18.2 | 81.8 | 11.5 | 88.5 |
| | genistin | 100 | 0 | 100 | 0 | 100 | 0 | 100 | 0 |
| | malonylglycitin | 100 | 0 | 21.7 | 78.3 | 15.5 | 84.5 | 14 | 86 |
| | malonyldaidzin | 100 | 0 | 49.2 | 50.8 | 39.9 | 60.1 | 38.5 | 61.5 |
| | malonylgenistin | 100 | 0 | 25.8 | 74.2 | 17.9 | 82.1 | 17.7 | 82.3 |
| | acetylglycitin | 100 | 0 | 2 | 98 | 2.1 | 97.9 | 2.5 | 97.5 |
| | acetyldaidzin | 100 | 0 | 10.4 | 89.6 | 3.8 | 96.2 | 3.8 | 96.2 |
| | acetylgenistin | 100 | 0 | 0.2 | 99.8 | 0.1 | 99.9 | 0.2 | 99.8 |
| Diglycosidase derived from A. fumigatus | glycitin | 100 | 0 | 99.5 | 0.5 | 100 | 0 | 100 | 0 |
| | daidzin | 99.1 | 0.9 | 92.9 | 7.1 | 85.3 | 14.7 | 75.2 | 24.8 |
| | genistin | 100 | 0 | 100 | 0 | 100 | 0 | 100 | 0 |
| | malonylglycitin | 100 | 0 | 99.6 | 0.4 | 99.2 | 0.8 | 98.6 | 1.4 |
| | malonyldaidzin | 100 | 0 | 90 | 10 | 79.5 | 20.5 | 67.7 | 32.3 |
| | malonylgenistin | 100 | 0 | 97.6 | 2.4 | 94.8 | 5.2 | 91.8 | 8.2 |
| | acetylglycitin | 100 | 0 | 94 | 6 | 86.5 | 13.5 | 77.3 | 22.7 |
| | acetyldaidzin | 100 | 0 | 73.9 | 26.1 | 52.8 | 47.2 | 33.5 | 66.5 |
| | acetylgenistin | 100 | 0 | 87.4 | 12.6 | 77.1 | 22.9 | 64.8 | 35.2 |
| β-Xylosidase derived from pectinase G | glycitin | 100 | 0 | 99.2 | 0.8 | 97.6 | 2.4 | 95.5 | 4.5 |
| | daidzin | 99.1 | 0.9 | 90.9 | 9.1 | 76 | 24 | 57.9 | 42.1 |
| | genistin | 100 | 0 | 98.5 | 1.5 | 98.2 | 1.8 | 98.2 | 1.8 |
| | malonylglycitin | 100 | 0 | 100 | 0 | 100 | 0 | 99.6 | 0.4 |
| | malonyldaidzin | 100 | 0 | 99.6 | 0.4 | 98.4 | 1.6 | 96.7 | 3.3 |
| | malonylgenistin | 100 | 0 | 100 | 0 | 99.4 | 0.6 | 98 | 2 |
| | acetylglycitin | 100 | 0 | 100 | 0 | 100 | 0 | 100 | 0 |
| | acetyldaidzin | 100 | 0 | 90.3 | 9.7 | 98.7 | 1.3 | 97.7 | 2.3 |
| | acetylgenistin | 100 | 0 | 100 | 0 | 99.8 | 0.2 | 99.5 | 0.5 |

TABLE 1-continued

| Purified enzyme | Substrate | Reaction time (h) | | | | | | | |
|---|---|---|---|---|---|---|---|---|---|
| | | 0 | | 1 | | 3 | | 6 | |
| | | glucoside | aglycon | glucoside | aglycon | glucoside | aglycon | glucoside | aglycon |
| β-Glucosidase derived from A. niger | glycitin | 100 | 0 | 50.5 | 49.5 | 11.7 | 88.3 | 4.5 | 95.5 |
| | daidzin | 100 | 0 | 0 | 100 | 0 | 100 | 0 | 100 |
| | genistin | 100 | 0 | 0 | 100 | 0 | 100 | 0 | 100 |
| | malonylglycitin | 100 | 0 | 98.8 | 1.2 | 95.6 | 4.4 | 90.9 | 9.1 |
| | malonyldaidzin | 100 | 0 | 95.5 | 4.5 | 90.7 | 9.3 | 84 | 16 |
| | malonylgenistin | 100 | 0 | 96.9 | 3.1 | 93 | 7 | 87.9 | 12.1 |
| | acetylglycitin | 100 | 0 | 100 | 0 | 99 | 1 | 98.1 | 1.9 |
| | acetyldaidzin | 100 | 0 | 95.6 | 4.4 | 93.6 | 6.4 | 91 | 9 |
| | acetylgenistin | 100 | 0 | 98.6 | 1.4 | 96.7 | 3.3 | 93.8 | 6.2 |
| β-Glucosidase derived from almond | glycitin | 100 | 0 | 98.4 | 1.6 | 98.1 | 1.9 | 98.1 | 1.9 |
| | daidzin | 99.1 | 0.9 | 90.9 | 9.1 | 89.2 | 10.8 | 88.7 | 11.3 |
| | genistin | 100 | 0 | 90.6 | 9.4 | 88.6 | 11.4 | 88.2 | 11.8 |
| | malonylglycitin | 100 | 0 | 100 | 0 | 100 | 0 | 100 | 0 |
| | malonyldaidzin | 100 | 0 | 100 | 0 | 100 | 0 | 100 | 0 |
| | malonylgenistin | 100 | 0 | 100 | 0 | 100 | 0 | 100 | 0 |
| | acetylglycitin | 100 | 0 | 100 | 0 | 100 | 0 | 100 | 0 |
| | acetyldaidzin | 99.8 | 0.2 | 99.5 | 0.5 | 99.4 | 0.6 | 99.4 | 0.6 |
| | acetylgenistin | 100 | 0 | 100 | 0 | 100 | 0 | 100 | 0 |

EXAMPLE 3

Influence of Free Glucose on Diglycosidase Activity

Purified diglycosidase was diluted with 20 mM acetate buffer of pH 4.0 to prepare a 0.75 AU/mL enzyme solution.

With a glucose solution was mixed 10 μL of each 2 mM substrate solution described in Example 2, and 20 mM acetate buffer of pH 4.0 was added thereto to be a liquid volume of 210 μL. Further, 40 μL of the enzyme solution was added and reaction was carried out at a final liquid volume of 250 μL. Adjustment of the glucose solution to be added allows glucose to exist in the reaction mixture in the range of 0 to 20%. The reaction was carried out at 55° C. and the existence of isoflavone glycosides and aglycon isoflavones was detected by HLPC at 0, 0.5, 1, and 3 hours of the reaction.

When the results were compared assuming that isolated aglycon amount at the glucose concentration of 0% and the reaction time of 0.5 hour is 100% using each isoflavone glycoside as the substrate, the converting efficiency of diglycosidase into aglycon isoflavone is hardly inhibited by the increase of free glucose concentration. To the contrary, increase of the converting efficiency was observed until 8% glucose concentration. Therefore, in the conversion into aglycon isoflavone by diglycosidase, no inhibition by glucose was observed up to 20% concentration (Table 2).

Moreover, β-glucosidase used in the conventional converting method into aglycon isoflavone is inhibited by glucose and large decrease of the reaction efficiency was observed, but diglycosidase of the invention was found to be hardly inhibited by glucose. Therefore, the amount, kind, and usage of phytogenic materials, which are starting materials for converting into aglycon isoflavone, are restricted in the case of the conventional glycosidase, but there is no such restriction in the case of diglycosidase of the invention and the efficiency of the conversion into isoflavone aglycon is remarkably enhanced.

TABLE 2

Isolation of isoflavone aglycons by diglycosidase in presence of glucose

| Glucose Concentration (%) | Isoflavone glycoside | | | | | | | |
|---|---|---|---|---|---|---|---|---|
| | glycitin | daidzin | acetylglycitin | acetylgenistin | acetyldaidzin | malonylglycitin | malonylgenistin | malonyldaidzin |
| 0 | 100 | 100 | 100 | 100 | 100 | 100 | 100 | 100 |
| 2 | 96 | 128.1 | 100.9 | 104.1 | 108.1 | 121.4 | 152 | 125.3 |
| 4 | 99.7 | 126 | 100.9 | 104.1 | 112.2 | 127.6 | 164.7 | 132.1 |
| 8 | 100.1 | 129.1 | 100.9 | 104.1 | 115.8 | 128.6 | 163.5 | 125.4 |
| 20 | 92.8 | 111.9 | 100.9 | 104.1 | 114.5 | 116.4 | 139.5 | 98.1 |

EXAMPLE 4

Examination of Temperature in the Conversion into Isoflavone Aglycons by Diglycosidase Using Soybean Materials Into 400 μL of 20 mM acetate buffer of pH 4.0 was suspended 50 mg of each of various soybean materials (roasted soy flour (manufactured by Fuji Shokuryo K.K.), soymilk (manufactured by Gitoh Shokuhin K.K.), defatted soybean (manufactured by Fuji Seiyu K.K.), concentrated soybean protein (manufactured by Fuji Seiyu K.K.)), whereby a substrate solution was prepared. Crude diglycosidase was diluted with 20 mM acetate buffer of pH 4.0 to be the glycosidase activity of 1.88 AU/mL. Fifty µL of the enzyme solution was mixed with the substrate solution and the whole was reacted at 80, 65, 55, 45, 37, or 30° C. at the total volume of 500 µL. To the reaction mixture was added 700 µL of ethanol after 0, 1, 3, and 6 hours of the reaction. After stirring and ultrasonication, the mixture was subjected to centrifugal separation at 15,000 rpm and 4° C. for 10 minutes. The supernatant was filtered through a filter and the existence of isoflavone glycosides and aglycon isoflavones contained in the reaction mixture was detected by HLPC.

The decomposition efficiency from isoflavone glycosides into aglycon isoflavones by an enzyme preparation containing diglycosidase activity was investigated during the treatment of 4 kinds of soybean materials (roasted soy flour, soymilk, concentrated soybean protein, defatted soybean) with the enzyme, the isoflavone compounds being separated into three groups. Namely, the conversion efficiency was analyzed upon three groups of glycitin family (glycitin, malonylglycitin, acetylglycitin, glycitein), genistin family (genistin, malonylgenistin, acetylgenistin, genistein), and daidzin family (daidzin, malonyldaidzin, malonyldaidzin, acetyldaidzin, daidzein (Tables 3 to 14).

TABLE 3

Decomposition efficiency of glycitin family in roasted soy flour

| Reaction temperature (° C.) | Heat treatment of enzyme | Reaction time (h) | Glycoside | | | Aglycon |
| --- | --- | --- | --- | --- | --- | --- |
| | | | glycitin | malonylglycitin | acetylglycitin | glycitein |
| 30 | no | 0 | 50.9 | not detected | 38.7 | 10.4 |
| | | 1 | 34.8 | not detected | 33.8 | 31.5 |
| | | 3 | not detected | not detected | 33.2 | 66.8 |
| | | 6 | not detected | not detected | 19.1 | 80.9 |
| | yes | 6 | 51.4 | not detected | 37.5 | 11.1 |
| 45 | no | 0 | 51.3 | not detected | 38.3 | 10.4 |
| | | 1 | 12.4 | not detected | 27.4 | 60.2 |
| | | 3 | 12.4 | not detected | 20.3 | 67.4 |
| | | 6 | 5.9 | not detected | 9.1 | 85.0 |
| | yes | 6 | 49.8 | not detected | 36.8 | 13.4 |
| 55 | no | 0 | 50.5 | not detected | 39.1 | 10.4 |
| | | 1 | not detected | not detected | 30.1 | 69.9 |
| | | 3 | not detected | not detected | 12.1 | 87.9 |
| | | 6 | not detected | not detected | 6.0 | 94.0 |
| | yes | 6 | 51.7 | not detected | 37.3 | 11.0 |
| 65 | no | 0 | 50.9 | not detected | 38.7 | 10.4 |
| | | 1 | not detected | not detected | 34.5 | 65.5 |
| | | 3 | not detected | not detected | 31.0 | 69.0 |
| | | 6 | not detected | not detected | 29.0 | 71.0 |
| | yes | 6 | 50.3 | not detected | 39.3 | 10.4 |
| 80 | no | 0 | 51.3 | not detected | 38.3 | 10.4 |
| | | 1 | 19.2 | not detected | 40.1 | 40.8 |
| | | 3 | 20.5 | not detected | 38.4 | 41.1 |
| | | 6 | 33.6 | not detected | 35.7 | 30.7 |
| | yes | 6 | 50.6 | not detected | 39.4 | 9.9 |

TABLE 4

Decomposition efficiency of genistin family in roasted soy flour

| Reaction temperature (° C.) | Heat treatment of enzyme | Reaction time (h) | Glycoside | | | Aglycon |
| --- | --- | --- | --- | --- | --- | --- |
| | | | genistin | malonylgenistin | acetylgenistin | genistein |
| 30 | no | 0 | 49.7 | not detected | 45.5 | 4.9 |
| | | 1 | 25.7 | not detected | 45.3 | 29.0 |
| | | 3 | 12.0 | not detected | 43.8 | 44.2 |
| | | 6 | 5.5 | not detected | 40.6 | 53.8 |
| | yes | 6 | 50.3 | not detected | 43.8 | 5.8 |
| 45 | no | 0 | 50.2 | not detected | 45.3 | 4.4 |
| | | 1 | 3.7 | not detected | 43.6 | 52.7 |
| | | 3 | 5.6 | not detected | 38.5 | 55.9 |
| | | 6 | 1.2 | not detected | 31.7 | 67.1 |
| | yes | 6 | 51.7 | not detected | 39.5 | 8.8 |
| 55 | no | 0 | 49.7 | not detected | 45.7 | 4.6 |
| | | 1 | 1.2 | not detected | 42.5 | 56.2 |
| | | 3 | not detected | not detected | 34.0 | 66.0 |
| | | 6 | not detected | not detected | 27.3 | 72.7 |
| | yes | 6 | 54.0 | not detected | 39.9 | 6.2 |

TABLE 4-continued

Decomposition efficiency of genistin family in roasted soy flour

| Reaction temperature (° C.) | Heat treatment of enzyme | Reaction time (h) | Glycoside | | | Aglycon |
|---|---|---|---|---|---|---|
| | | | genistin | malonylgenistin | acetylgenistin | genistein |
| 65 | no | 0 | 49.7 | not detected | 45.5 | 4.9 |
| | | 1 | not detected | not detected | 43.6 | 56.4 |
| | | 3 | not detected | not detected | 40.5 | 59.5 |
| | | 6 | not detected | not detected | 38.8 | 61.2 |
| | yes | 6 | 50.7 | not detected | 44.3 | 5.0 |
| 80 | no | 0 | 50.2 | not detected | 45.3 | 4.4 |
| | | 1 | 7.8 | not detected | 48.5 | 43.6 |
| | | 3 | 9.1 | not detected | 48.2 | 42.7 |
| | | 6 | 18.4 | not detected | 47.7 | 33.9 |
| | yes | 6 | 52.2 | not detected | 43.4 | 4.3 |

TABLE 5

Decomposition efficiency of daidzin family in roasted soy flour

| Reaction temperature (° C.) | Heat treatment of enzyme | Reaction time (h) | Glycoside | | | Aglycon |
|---|---|---|---|---|---|---|
| | | | daidzin | malonyldaidzin | acetyldaidzin | daidzein |
| 35 | no | 0 | 48.6 | not detected | 47.8 | 3.6 |
| | | 1 | 11.7 | not detected | 46.9 | 41.4 |
| | | 3 | not detected | not detected | 45.3 | 54.7 |
| | | 6 | not detected | not detected | 39.6 | 60.4 |
| | yes | 6 | 50.3 | not detected | 43.8 | 5.8 |
| 45 | no | 0 | 48.6 | not detected | 47.7 | 3.7 |
| | | 1 | 3.6 | not detected | 42.9 | 53.5 |
| | | 3 | 2.7 | not detected | 37.9 | 59.4 |
| | | 6 | 5.4 | not detected | 28.5 | 66.2 |
| | yes | 6 | 49.4 | not detected | 42.5 | 8.1 |
| 55 | no | 0 | 48.8 | not detected | 47.5 | 3.7 |
| | | 1 | not detected | not detected | 42.8 | 57.2 |
| | | 3 | not detected | not detected | 32.5 | 67.5 |
| | | 6 | not detected | not detected | 26.7 | 73.3 |
| | yes | 6 | 51.1 | not detected | 43.6 | 5.3 |
| 65 | no | 0 | 48.6 | not detected | 47.8 | 3.6 |
| | | 1 | not detected | not detected | 43.7 | 56.3 |
| | | 3 | not detected | not detected | 40.2 | 59.8 |
| | | 6 | not detected | not detected | 37.8 | 62.2 |
| | yes | 6 | 49.7 | not detected | 46.1 | 4.2 |
| 80 | no | 0 | 48.6 | not detected | 47.7 | 3.7 |
| | | 1 | 3.2 | not detected | 49.1 | 47.7 |
| | | 3 | 4.4 | not detected | 47.9 | 47.7 |
| | | 6 | 12.5 | not detected | 46.7 | 40.8 |
| | yes | 6 | 51.3 | not detected | 45.0 | 3.8 |

TABLE 6

Decomposition efficiency of glycitin family in soymilk

| Reaction temperature (° C.) | Heat treatment of enzyme | Reaction time (h) | Glycoside | | | Aglycon |
|---|---|---|---|---|---|---|
| | | | glycitin | malonylglycitin | acetylglycitin | glycitein |
| 30 | no | 0 | 43.9 | 48.0 | not detected | 8.1 |
| | | 1 | not detected | 51.0 | not detected | 49.0 |
| | | 3 | not detected | 39.6 | not detected | 60.4 |
| | | 6 | not detected | 28.4 | not detected | 71.6 |
| | yes | 6 | 44.5 | 47.7 | not detected | 7.9 |

TABLE 6-continued

Decomposition efficiency of glycitin family in soymilk

| Reaction temperature (° C.) | Heat treatment of enzyme | Reaction time (h) | Glycoside | | | Aglycon |
|---|---|---|---|---|---|---|
| | | | glycitin | malonylglycitin | acetylglycitin | glycitein |
| 45 | no | 0 | 42.6 | 49.1 | not detected | 8.2 |
| | | 1 | not detected | 46.2 | not detected | 53.8 |
| | | 3 | not detected | 29.9 | not detected | 70.1 |
| | | 6 | not detected | 15.3 | not detected | 84.7 |
| | yes | 6 | 45.4 | 47.2 | not detected | 7.4 |
| 55 | no | 0 | 47.8 | 44.6 | not detected | 7.6 |
| | | 1 | not detected | 39.1 | not detected | 60.9 |
| | | 3 | not detected | 27.7 | not detected | 72.3 |
| | | 6 | not detected | 16.5 | not detected | 83.5 |
| | yes | 6 | 53.5 | 39.9 | not detected | 6.7 |
| 65 | no | 0 | 43.9 | 48.0 | not detected | 8.1 |
| | | 1 | not detected | 42.4 | not detected | 57.6 |
| | | 3 | not detected | 34.3 | not detected | 65.7 |
| | | 6 | not detected | 25.5 | not detected | 74.5 |
| | yes | 6 | 56.8 | 36.0 | not detected | 7.2 |
| 80 | no | 0 | 42.6 | 49.1 | not detected | 8.2 |
| | | 1 | 10.7 | 43.6 | not detected | 45.7 |
| | | 3 | 22.5 | 32.6 | not detected | 44.9 |
| | | 6 | 44.2 | 21.3 | not detected | 34.4 |
| | yes | 6 | 71.4 | 19.3 | not detected | 9.3 |

TABLE 7

Decomposition efficiency of genistin family in soymilk

| Reaction temperature (° C.) | Heat treatment of enzyme | Reaction time (h) | Glycoside | | | Aglycon |
|---|---|---|---|---|---|---|
| | | | genistin | malonylgenistin | acetylgenistin | genistein |
| 30 | no | 0 | 30.7 | 58.5 | 0.9 | 10.0 |
| | | 1 | not detected | 56.5 | not detected | 43.5 |
| | | 3 | not detected | 47.9 | not detected | 52.1 |
| | | 6 | not detected | 36.1 | not detected | 63.9 |
| | yes | 6 | 31.2 | 57.7 | 0.9 | 10.1 |
| 45 | no | 0 | 31.0 | 57.8 | 0.9 | 10.3 |
| | | 1 | not detected | 49.4 | not detected | 50.6 |
| | | 3 | not detected | 34.7 | not detected | 65.3 |
| | | 6 | not detected | 20.7 | not detected | 79.3 |
| | yes | 6 | 34.4 | 57.2 | 0.6 | 7.9 |
| 55 | no | 0 | 31.6 | 59.1 | 0.6 | 8.7 |
| | | 1 | not detected | 46.9 | not detected | 53.1 |
| | | 3 | not detected | 32.5 | not detected | 67.5 |
| | | 6 | not detected | 20.4 | not detected | 79.6 |
| | yes | 6 | 37.4 | 53.3 | 0.7 | 8.6 |
| 65 | no | 0 | 30.7 | 58.5 | 0.9 | 10.0 |
| | | 1 | not detected | 48.9 | not detected | 51.1 |
| | | 3 | not detected | 40.6 | not detected | 59.4 |
| | | 6 | not detected | 31.8 | not detected | 68.2 |
| | yes | 6 | 44.4 | 44.6 | 1.1 | 9.9 |
| 80 | no | 0 | 31.0 | 57.8 | 0.9 | 10.3 |
| | | 1 | 10.6 | 50.4 | 0.9 | 38.0 |
| | | 3 | 24.3 | 37.7 | 1.0 | 37.0 |
| | | 6 | 43.9 | 24.1 | 2.3 | 29.6 |
| | yes | 6 | 64.5 | 22.9 | 2.5 | 10.1 |

TABLE 8

Decomposition efficiency of daidzin family in soymilk

| Reaction temperature (° C.) | Heat treatment of enzyme | Reaction time (h) | Glycoside | | | Aglycon |
|---|---|---|---|---|---|---|
| | | | daidzin | malonyldaidzin | acetyldaidzin | daidzein |
| 30 | no | 0 | 34.1 | 56.8 | not detected | 9.1 |
| | | 1 | not detected | 58.2 | not detected | 41.8 |
| | | 3 | not detected | 52.8 | not detected | 47.2 |
| | | 6 | not detected | 46.2 | not detected | 53.8 |
| | yes | 6 | 34.8 | 56.1 | not detected | 9.1 |
| 45 | no | 0 | 33.9 | 57.2 | not detected | 8.9 |
| | | 1 | 6.8 | 50.2 | not detected | 43.0 |
| | | 3 | 6.9 | 41.1 | not detected | 52.0 |
| | | 6 | 6.9 | 30.2 | not detected | 62.8 |
| | yes | 6 | 36.0 | 55.8 | not detected | 8.2 |
| 55 | no | 0 | 34.2 | 57.3 | not detected | 8.6 |
| | | 1 | not detected | 50.9 | not detected | 49.1 |
| | | 3 | not detected | 41.1 | not detected | 58.9 |
| | | 6 | not detected | 31.1 | not detected | 68.9 |
| | yes | 6 | 40.7 | 50.8 | not detected | 8.6 |
| 65 | no | 0 | 34.1 | 56.8 | not detected | 9.1 |
| | | 1 | not detected | 51.7 | not detected | 48.3 |
| | | 3 | not detected | 43.9 | not detected | 56.1 |
| | | 6 | not detected | 35.3 | not detected | 64.7 |
| | yes | 6 | 48.7 | 42.4 | not detected | 8.8 |
| 80 | no | 0 | 33.9 | 57.2 | not detected | 8.9 |
| | | 1 | 8.9 | 50.8 | not detected | 40.3 |
| | | 3 | 23.9 | 36.4 | not detected | 39.7 |
| | | 6 | 42.9 | 23.0 | not detected | 34.1 |
| | yes | 6 | 69.5 | 21.8 | not detected | 8.8 |

TABLE 9

Decomposition efficiency of glycitin family in concentrated soybean protein

| Reaction temperature (° C.) | Heat treatment of enzyme | Reaction time (h) | Glycoside | | | Aglycon |
|---|---|---|---|---|---|---|
| | | | glycitin | malonylglycitin | acetylglycitin | glycitein |
| 30 | no | 0 | 52.2 | 0.4 | 36.0 | 11.4 |
| | | 1 | 47.1 | 0.5 | 35.0 | 17.5 |
| | | 3 | 39.1 | 0.5 | 33.4 | 26.9 |
| | | 6 | 28.4 | 0.5 | 30.8 | 40.3 |
| | yes | 6 | 52.8 | 0.4 | 35.4 | 11.3 |
| 45 | no | 0 | 52.3 | 0.4 | 35.9 | 11.4 |
| | | 1 | 30.2 | 0.6 | 34.1 | 35.2 |
| | | 3 | 18.8 | 0.6 | 31.0 | 49.6 |
| | | 6 | 7.5 | 0.6 | 27.1 | 64.9 |
| | yes | 6 | 53.2 | 0.5 | 35.0 | 11.3 |
| 55 | no | 0 | 52.3 | 0.4 | 36.0 | 11.2 |
| | | 1 | 14.2 | 0.5 | 33.9 | 51.4 |
| | | 3 | not detected | 0.5 | 29.8 | 69.7 |
| | | 6 | not detected | 0.5 | 26.8 | 72.7 |
| | yes | 6 | 52.9 | 0.4 | 35.3 | 11.3 |
| 65 | no | 0 | 52.2 | 0.4 | 36.0 | 11.4 |
| | | 1 | 5.2 | 0.5 | 35.7 | 58.6 |
| | | 3 | not detected | 0.5 | 35.5 | 64.0 |
| | | 6 | not detected | 0.4 | 35.8 | 63.8 |
| | yes | 6 | 52.5 | 0.4 | 35.7 | 11.4 |
| 80 | no | 0 | 52.3 | 0.4 | 35.9 | 11.4 |
| | | 1 | 39.7 | 0.4 | 36.0 | 23.8 |
| | | 3 | 40.5 | 0.4 | 35.7 | 23.4 |
| | | 6 | 41.7 | 0.3 | 35.2 | 22.8 |
| | yes | 6 | 53.6 | 0.3 | 34.8 | 11.4 |

TABLE 10

Decomposition efficiency of genistin family in concentrated soybean protein

| Reaction temperature (° C.) | Heat treatment of enzyme | Reaction time (h) | Glycoside | | | Aglycon |
|---|---|---|---|---|---|---|
| | | | genistin | malonylgenistin | acetylgenistin | genistein |
| 30 | no | 0 | 49.8 | not detected | 43.1 | 7.1 |
| | | 1 | 41.1 | not detected | 43.2 | 15.7 |
| | | 3 | 30.3 | not detected | 43.0 | 26.7 |
| | | 6 | 19.7 | not detected | 42.5 | 37.8 |
| | yes | 6 | 51.8 | not detected | 41.5 | 6.7 |
| 45 | no | 0 | 49.7 | not detected | 43.0 | 7.2 |
| | | 1 | 22.2 | not detected | 42.8 | 35.0 |
| | | 3 | 15.6 | not detected | 41.0 | 43.4 |
| | | 6 | 5.3 | not detected | 39.6 | 55.1 |
| | yes | 6 | 54.5 | not detected | 38.9 | 6.5 |
| 55 | no | 0 | 50.1 | not detected | 42.9 | 7.0 |
| | | 1 | 7.0 | not detected | 43.1 | 49.8 |
| | | 3 | 0.8 | not detected | 41.1 | 58.1 |
| | | 6 | not detected | not detected | 39.0 | 61.0 |
| | yes | 6 | 52.3 | not detected | 41.1 | 6.6 |
| 65 | no | 0 | 49.8 | not detected | 43.1 | 7.1 |
| | | 1 | not detected | not detected | 45.2 | 54.8 |
| | | 3 | not detected | not detected | 44.0 | 56.0 |
| | | 6 | not detected | not detected | 43.4 | 56.6 |
| | yes | 6 | 50.8 | not detected | 42.3 | 6.9 |
| 80 | no | 0 | 49.7 | not detected | 43.0 | 7.2 |
| | | 1 | 29.6 | not detected | 44.0 | 26.4 |
| | | 3 | 30.3 | not detected | 43.6 | 26.1 |
| | | 6 | 32.3 | not detected | 43.4 | 24.3 |
| | yes | 6 | 51.9 | not detected | 41.4 | 6.7 |

TABLE 11

Decomposition efficiency of daidzin family in concentrated soybean protein

| Reaction temperature (° C.) | Heat treatment of enzyme | Reaction time (h) | Glycoside | | | Aglycon |
|---|---|---|---|---|---|---|
| | | | daidzin | malonyldaidzin | acetyldaidzin | daidzein |
| 30 | no | 0 | 52.3 | not detected | 44.6 | 3.0 |
| | | 1 | 29.5 | not detected | 44.4 | 26.2 |
| | | 3 | 13.4 | not detected | 43.9 | 42.7 |
| | | 6 | 4.0 | not detected | 43.5 | 52.5 |
| | yes | 6 | 54.5 | not detected | 42.3 | 3.2 |
| 45 | no | 0 | 52.4 | not detected | 44.5 | 3.1 |
| | | 1 | 10.6 | not detected | 44.1 | 45.3 |
| | | 3 | 9.6 | not detected | 41.5 | 48.8 |
| | | 6 | 1.7 | not detected | 42.9 | 55.5 |
| | yes | 6 | 94.3 | not detected | 0.0 | 5.7 |
| 55 | no | 0 | 52.5 | not detected | 44.5 | 3.0 |
| | | 1 | 1.0 | not detected | 44.0 | 55.0 |
| | | 3 | not detected | not detected | 40.6 | 59.4 |
| | | 6 | not detected | not detected | 37.7 | 62.3 |
| | yes | 6 | 54.6 | not detected | 42.3 | 3.2 |
| 65 | no | 0 | 52.3 | not detected | 44.6 | 3.0 |
| | | 1 | 1.8 | not detected | 44.3 | 53.9 |
| | | 3 | 1.7 | not detected | 42.9 | 55.4 |
| | | 6 | 1.7 | not detected | 41.6 | 56.7 |
| | yes | 6 | 53.2 | not detected | 43.6 | 3.2 |
| 80 | no | 0 | 52.4 | not detected | 44.5 | 3.1 |
| | | 1 | 22.6 | not detected | 45.5 | 31.9 |
| | | 3 | 23.3 | not detected | 44.7 | 32.0 |
| | | 6 | 25.5 | not detected | 43.8 | 30.7 |
| | yes | 6 | 54.5 | not detected | 42.3 | 3.2 |

TABLE 12

Decomposition efficiency of glycitin family in defatted soybean

| Reaction temperature (° C.) | Heat treatment of enzyme | Reaction time (h) | Glycoside | | | Aglycon |
|---|---|---|---|---|---|---|
| | | | glycitin | malonylglycitin | acetylglycitin | glycitein |
| 30 | no | 0 | not detected | 61.3 | not detected | 38.7 |
| | | 1 | not detected | 48.3 | not detected | 51.7 |
| | | 3 | not detected | 44.6 | not detected | 55.4 |
| | | 6 | not detected | 45.6 | not detected | 54.4 |
| | yes | 6 | not detected | 45.1 | not detected | 54.9 |
| 45 | no | 0 | not detected | 65.2 | not detected | 34.8 |
| | | 1 | not detected | 44.3 | not detected | 55.7 |
| | | 3 | not detected | 44.8 | not detected | 55.2 |
| | | 6 | not detected | 41.0 | not detected | 59.0 |
| | yes | 6 | not detected | 44.2 | not detected | 55.8 |
| 55 | no | 0 | not detected | 61.3 | not detected | 38.7 |
| | | 1 | not detected | 44.8 | not detected | 55.2 |
| | | 3 | not detected | 42.6 | not detected | 57.4 |
| | | 6 | not detected | 42.7 | not detected | 57.3 |
| | yes | 6 | not detected | 45.5 | not detected | 54.5 |
| 65 | no | 0 | not detected | 65.2 | not detected | 34.8 |
| | | 1 | not detected | 45.3 | not detected | 54.7 |
| | | 3 | not detected | 42.1 | not detected | 57.9 |
| | | 6 | not detected | 40.0 | not detected | 60.0 |
| | yes | 6 | not detected | 48.8 | not detected | 51.2 |
| 80 | no | 0 | not detected | 65.2 | not detected | 34.8 |
| | | 1 | not detected | 46.1 | not detected | 53.9 |
| | | 3 | not detected | 45.0 | not detected | 55.0 |
| | | 6 | not detected | 40.3 | not detected | 59.7 |
| | yes | 6 | not detected | 48.1 | not detected | 51.9 |

TABLE 13

Decomposition efficiency of genistin family in defatted soybean

| Reaction temperature (° C.) | Heat treatment of enzyme | Reaction time (h) | Glycoside | | | Aglycon |
|---|---|---|---|---|---|---|
| | | | genistin | malonylgenistin | acetylgenistin | genistein |
| 30 | no | 0 | 38.0 | 47.0 | 1.7 | 13.3 |
| | | 1 | not detected | 51.3 | 1.3 | 47.4 |
| | | 3 | not detected | 49.1 | 0.7 | 50.2 |
| | | 6 | 7.6 | 45.6 | 0.1 | 46.6 |
| | yes | 6 | not detected | 49.5 | 0.4 | 50.2 |
| 45 | no | 0 | 37.0 | 47.0 | 1.5 | 14.5 |
| | | 1 | 0.9 | 49.0 | 0.8 | 49.2 |
| | | 3 | 1.0 | 46.8 | 0.3 | 51.8 |
| | | 6 | 1.0 | 44.2 | 0.2 | 54.6 |
| | yes | 6 | 1.3 | 48.1 | 0.2 | 50.4 |
| 55 | no | 0 | 38.0 | 47.0 | 1.7 | 13.3 |
| | | 1 | 0.0 | 48.8 | 0.7 | 50.5 |
| | | 3 | 0.0 | 46.1 | 0.2 | 53.7 |
| | | 6 | 0.0 | 43.4 | 0.1 | 56.5 |
| | yes | 6 | 0.0 | 47.8 | 0.4 | 51.9 |
| 65 | no | 0 | 37.0 | 47.0 | 1.5 | 14.5 |
| | | 1 | 0.0 | 48.9 | 1.2 | 49.9 |
| | | 3 | 1.8 | 45.2 | 1.2 | 51.8 |
| | | 6 | 3.3 | 41.1 | 1.1 | 54.5 |
| | yes | 6 | 28.2 | 39.7 | 1.3 | 30.7 |
| 80 | no | 0 | 37.0 | 47.0 | 1.5 | 14.5 |
| | | 1 | 9.6 | 43.8 | 1.8 | 44.9 |
| | | 3 | 22.1 | 32.5 | 2.1 | 43.3 |
| | | 6 | 35.3 | 20.9 | 2.5 | 41.3 |
| | yes | 6 | 57.8 | 20.1 | 2.4 | 19.6 |

TABLE 14

Decomposition efficiency of daidzin family in defatted soybean

| Reaction temperature (° C.) | Heat treatment of enzyme | Reaction time (h) | Glycoside | | | Aglycon |
|---|---|---|---|---|---|---|
| | | | daidzin | malonyldaidzin | acetyldaidzin | daidzein |
| 30 | no | 0 | 42.2 | 43.3 | not detected | 14.5 |
| | | 1 | not detected | 46.6 | not detected | 53.4 |
| | | 3 | not detected | 45.2 | not detected | 54.8 |
| | | 6 | not detected | 45.1 | not detected | 54.9 |
| | yes | 6 | not detected | 45.4 | not detected | 54.6 |
| 45 | no | 0 | 40.5 | 43.3 | not detected | 16.2 |
| | | 1 | not detected | 45.5 | not detected | 54.5 |
| | | 3 | not detected | 43.7 | not detected | 56.3 |
| | | 6 | not detected | 41.7 | not detected | 58.3 |
| | yes | 6 | not detected | 44.3 | not detected | 55.7 |
| 55 | no | 0 | 42.2 | 43.3 | not detected | 14.5 |
| | | 1 | not detected | 45.0 | not detected | 55.0 |
| | | 3 | not detected | 42.7 | not detected | 57.3 |
| | | 6 | not detected | 40.3 | not detected | 59.7 |
| | yes | 6 | not detected | 44.1 | not detected | 55.9 |
| 65 | no | 0 | 40.5 | 43.3 | not detected | 16.2 |
| | | 1 | not detected | 44.7 | not detected | 55.3 |
| | | 3 | not detected | 41.6 | not detected | 58.4 |
| | | 6 | not detected | 37.3 | not detected | 62.7 |
| | yes | 6 | 32.8 | 35.2 | not detected | 32.0 |
| 80 | no | 0 | 40.5 | 43.3 | not detected | 16.2 |
| | | 1 | 7.8 | 39.8 | not detected | 52.4 |
| | | 3 | 19.2 | 28.8 | not detected | 52.0 |
| | | 6 | 30.4 | 17.8 | not detected | 51.7 |
| | yes | 6 | 60.9 | 17.4 | not detected | 21.7 |

All three groups of isoflavone glucosides were decomposed at all the temperature ranges tested, and promptly at 37 to 65° C., particularly 55° C. Furthermore, in defatted soybean, endogenous β-glucosidase also participates in the decomposition. It is revealed that the decomposition of modified glucoside glycosides, most of which is considered to occur by the action of diglycosidase, easily occurs at a temperature of 37 to 55° C. Among three groups of aglycon isoflavones, maximum isolation of aglycons was observed in the reaction at 55° C. for 6 hours. In the case of soy flour, glycitein was about 94%, genistein about 74%, and daidzein about 73%. In the case of soymilk, glycitein was about 84%, genistein about 80%, and daidzein about 70%. In the case of concentrated soybean protein, glycitein was about 73%, genistein about 61%, and daidzein about 62%. In the case of defatted soybean, glycitein was about 57%, genistein about 57%, and daidzein about 60%.

From these results, it was revealed that the decomposition of modified glucoside glycosides by diglycosidase efficiently occurred at a temperature of 37 to 65° C., particularly around 55° C.

EXAMPLE 5

Examination of pH in the Conversion into Isoflavone Aglycons by Diglycosidase Using Soybean Materials A substrate solution of 450 μL was prepared by suspending 50 mg of each soybean material (roasted soy flour (manufactured by Fuji Shokuryo K.K.), soymilk (manufactured by Gitoh Shokuhin K.K.), defatted soybean (manufactured by Fuji Seiyu K.K.), concentrated soybean protein (manufactured by Fuji Seiyu K.K.)), and adjusting the pH to 2 to 11 with hydrochloric acid or sodium hydroxide. Each enzyme solution of pH 2–11 wherein diglycosidase activity of crude diglycosidase was adjusted to 1.88 AU/mL was added thereto in an amount of 50 μL and the whole was reacted at 55° C. at the total volume of 500 μL. To the reaction mixture was added 700 μL of ethanol after 0, 1, 3, and 6 hours of the reaction. After stirring and ultrasonication, the mixture was subjected to centrifugal separation at 15,000 rpm and 4° C. for 10 minutes. The supernatant was filtered through a filter and the existence of isoflavone glycosides and aglycon isoflavones contained in the reaction mixture was detected by HLPC (Tables 15 to 26).

TABLE 15

Decomposition efficiency of glycitin family in roasted soy flour

| Reaction pH | Heat treatment of enzyme | Reaction time (h) | Glycoside | | | Aglycon |
|---|---|---|---|---|---|---|
| | | | glycitin | malonylglycitin | acetylglycitin | glycitein |
| pH2 | no | 0 | 56.8 | not detected | 35.3 | 7.9 |
| | | 1 | 56.6 | not detected | 34.0 | 9.4 |
| | | 3 | 56.3 | not detected | 34.2 | 9.5 |
| | | 6 | 54.4 | not detected | 35.5 | 10.1 |
| | yes | 6 | 54.4 | not detected | 35.2 | 10.4 |

TABLE 15-continued

Decomposition efficiency of glycitin family in roasted soy flour

| Reaction pH | Heat treatment of enzyme | Reaction time (h) | Glycoside glycitin | Glycoside malonylglycitin | Glycoside acetylglycitin | Aglycon glycitein |
|---|---|---|---|---|---|---|
| pH3 | no | 0 | 56.8 | not detected | 35.3 | 7.9 |
|  |  | 1 | not detected | not detected | 38.7 | 61.3 |
|  |  | 3 | not detected | not detected | 30.8 | 69.2 |
|  |  | 6 | not detected | not detected | 31.7 | 68.3 |
|  | yes | 6 | 55.1 | not detected | 35.6 | 9.3 |
| pH4 | no | 0 | 56.6 | not detected | 34.8 | 8.6 |
|  |  | 1 | not detected | not detected | 18.8 | 81.2 |
|  |  | 3 | not detected | not detected | 8.2 | 91.8 |
|  |  | 6 | not detected | not detected | not detected | 100.0 |
|  | yes | 6 | 55.1 | not detected | 35.9 | 9.0 |
| pH5 | no | 0 | 56.6 | not detected | 34.8 | 8.6 |
|  |  | 1 | not detected | not detected | 22.9 | 77.1 |
|  |  | 3 | not detected | not detected | 6.5 | 93.5 |
|  |  | 6 | not detected | not detected | not detected | 100.0 |
|  | yes | 6 | 55.4 | not detected | 35.2 | 9.4 |
| pH6.5 | no | 0 | 55.9 | not detected | 35.4 | 8.8 |
|  |  | 1 | not detected | not detected | 35.0 | 65.0 |
|  |  | 3 | not detected | not detected | 19.7 | 80.3 |
|  |  | 6 | not detected | not detected | 11.9 | 88.1 |
|  | yes | 6 | 54.8 | not detected | 35.4 | 9.8 |
| pH8.5 | no | 0 | 59.4 | not detected | 31.0 | 9.6 |
|  |  | 1 | 39.4 | not detected | 32.4 | 28.2 |
|  |  | 3 | 29.3 | not detected | 30.6 | 40.1 |
|  |  | 6 | 22.4 | not detected | 30.2 | 47.4 |
|  | yes | 6 | 59.2 | not detected | 31.7 | 9.1 |

TABLE 16

Decomposition efficiency of genistin family in roasted soy flour

| Reaction pH | Heat treatment of enzyme | Reaction time (h) | Glycoside genistin | Glycoside malonylgenistin | Glycoside acetylgenistin | Aglycon genistein |
|---|---|---|---|---|---|---|
| pH2 | no | 0 | 50.0 | not detected | 45.2 | 4.8 |
|  |  | 1 | 49.7 | not detected | 45.0 | 5.3 |
|  |  | 3 | 50.7 | not detected | 43.1 | 6.2 |
|  |  | 6 | 52.7 | not detected | 40.7 | 6.5 |
|  | yes | 6 | 52.8 | not detected | 41.2 | 6.0 |
| pH3 | no | 0 | 50.0 | not detected | 45.2 | 4.8 |
|  |  | 1 | 3.4 | not detected | 45.2 | 51.4 |
|  |  | 3 | not detected | not detected | 41.9 | 58.1 |
|  |  | 6 | not detected | not detected | 43.5 | 56.5 |
|  | yes | 6 | 49.9 | not detected | 45.1 | 5.0 |
| pH4 | no | 0 | 49.9 | not detected | 45.4 | 4.7 |
|  |  | 1 | not detected | not detected | 36.3 | 63.7 |
|  |  | 3 | not detected | not detected | 23.4 | 76.6 |
|  |  | 6 | not detected | not detected | 13.4 | 86.6 |
|  | yes | 6 | 50.2 | not detected | 45.4 | 4.4 |
| pH5 | no | 0 | 49.9 | not detected | 45.4 | 4.7 |
|  |  | 1 | not detected | not detected | 39.9 | 60.1 |
|  |  | 3 | not detected | not detected | 26.9 | 73.1 |
|  |  | 6 | not detected | not detected | 17.6 | 82.4 |
|  | yes | 6 | 52.6 | not detected | 42.0 | 5.3 |
| pH6.5 | no | 0 | 49.4 | not detected | 45.8 | 4.8 |
|  |  | 1 | not detected | not detected | 45.3 | 54.7 |
|  |  | 3 | not detected | not detected | 38.8 | 61.2 |
|  |  | 6 | not detected | not detected | 34.0 | 66.0 |
|  | yes | 6 | 54.8 | not detected | 39.2 | 6.0 |
| pH8.5 | no | 0 | 55.8 | not detected | 39.5 | 4.6 |
|  |  | 1 | 28.7 | not detected | 39.5 | 31.8 |
|  |  | 3 | 19.2 | not detected | 39.2 | 41.6 |
|  |  | 6 | 14.5 | not detected | 37.3 | 48.2 |
|  | yes | 6 | 59.5 | not detected | 35.2 | 5.3 |

TABLE 17

Decomposition efficiency of daidzin family in roasted soy flour

| Reaction pH | Heat treatment of enzyme | Reaction time (h) | Glycoside daidzin | malonyldaidzin | acetyldaidzin | Aglycon daidzein |
|---|---|---|---|---|---|---|
| pH2 | no | 0 | 49.1 | not detected | 47.4 | 3.5 |
| | | 1 | 47.6 | not detected | 46.9 | 5.4 |
| | | 3 | 50.3 | not detected | 45.0 | 4.8 |
| | | 6 | 53.1 | not detected | 42.4 | 4.5 |
| | yes | 6 | 53.8 | not detected | 42.4 | 3.8 |
| pH3 | no | 0 | 49.1 | not detected | 47.4 | 3.5 |
| | | 1 | not detected | not detected | 46.0 | 54.0 |
| | | 3 | not detected | not detected | 39.6 | 60.4 |
| | | 6 | not detected | not detected | 40.7 | 59.3 |
| | yes | 6 | 49.0 | not detected | 47.4 | 3.7 |
| pH4 | no | 0 | 48.7 | not detected | 47.7 | 3.5 |
| | | 1 | not detected | not detected | 34.4 | 65.6 |
| | | 3 | not detected | not detected | 20.5 | 79.5 |
| | | 6 | not detected | not detected | 11.1 | 88.9 |
| | yes | 6 | 48.6 | not detected | 47.9 | 3.5 |
| pH5 | no | 0 | 48.7 | not detected | 47.7 | 3.5 |
| | | 1 | not detected | not detected | 38.5 | 61.5 |
| | | 3 | not detected | not detected | 24.7 | 75.3 |
| | | 6 | not detected | not detected | 15.2 | 84.8 |
| | yes | 6 | 50.6 | not detected | 45.0 | 4.4 |
| pH6.5 | no | 0 | 48.4 | not detected | 48.2 | 3.4 |
| | | 1 | not detected | not detected | 45.4 | 54.6 |
| | | 3 | not detected | not detected | 39.2 | 60.8 |
| | | 6 | not detected | not detected | 34.4 | 65.6 |
| | yes | 6 | 51.9 | not detected | 43.4 | 4.7 |
| pH8.5 | no | 0 | 54.1 | not detected | 42.1 | 3.8 |
| | | 1 | 20.4 | not detected | 42.7 | 36.9 |
| | | 3 | 13.3 | not detected | 40.3 | 46.4 |
| | | 6 | 10.2 | not detected | 38.0 | 51.8 |
| | yes | 6 | 58.8 | not detected | 37.3 | 3.9 |

TABLE 18

Decomposition efficiency of glycitin family in soymilk

| Reaction pH | Heat treatment of enzyme | Reaction time (h) | Glycoside glycitin | malonylglycitin | acetylglycitin | Aglycon glycitein |
|---|---|---|---|---|---|---|
| pH2.3 | no | 0 | 50.2 | 42.6 | not detected | 7.2 |
| | | 1 | not detected | 51.3 | not detected | 48.7 |
| | | 3 | not detected | 47.7 | not detected | 52.3 |
| | | 6 | not detected | 46.5 | not detected | 53.5 |
| | yes | 6 | 51.7 | 41.3 | not detected | 6.9 |
| pH3.5 | no | 0 | 50.2 | 42.6 | not detected | 7.2 |
| | | 1 | not detected | 21.9 | not detected | 78.1 |
| | | 3 | not detected | not detected | not detected | 100.0 |
| | | 6 | not detected | not detected | not detected | 100.0 |
| | yes | 6 | 54.2 | 38.2 | not detected | 7.6 |
| pH4.8 | no | 0 | 50.7 | 43.2 | not detected | 6.2 |
| | | 1 | not detected | 37.0 | not detected | 63.0 |
| | | 3 | not detected | 21.1 | not detected | 78.9 |
| | | 6 | not detected | 8.3 | not detected | 91.7 |
| | yes | 6 | 54.3 | 39.2 | not detected | 6.5 |
| pH6.2 | no | 0 | 50.7 | 43.2 | not detected | 6.2 |
| | | 1 | not detected | 46.4 | not detected | 53.6 |
| | | 3 | not detected | 34.5 | not detected | 65.5 |
| | | 6 | not detected | 29.6 | not detected | 70.4 |
| | yes | 6 | 54.2 | 37.6 | not detected | 8.2 |
| pH7.2 | no | 0 | 50.0 | 43.9 | not detected | 6.1 |
| | | 1 | not detected | 48.8 | not detected | 51.2 |
| | | 3 | not detected | 46.2 | not detected | 53.8 |
| | | 6 | not detected | 41.6 | not detected | 58.4 |
| | yes | 6 | 56.9 | 37.5 | not detected | 5.6 |

TABLE 18-continued

Decomposition efficiency of glycitin family in soymilk

| Reaction pH | Heat treatment of enzyme | Reaction time (h) | Glycoside | | | Aglycon |
|---|---|---|---|---|---|---|
| | | | glycitin | malonylglycitin | acetylglycitin | glycitein |
| pH11.6 | no | 0 | 54.3 | 39.4 | not detected | 6.2 |
| | | 1 | not detected | 50.4 | not detected | 49.6 |
| | | 3 | not detected | 46.5 | not detected | 53.5 |
| | | 6 | not detected | 44.0 | not detected | 56.0 |
| | yes | 6 | 59.7 | 34.4 | not detected | 5.8 |

15

TABLE 19

Decomposition efficiency of genistin family in soymilk

| Reaction pH | Heat treatment of enzyme | Reaction time (h) | Glycoside | | | Aglycon |
|---|---|---|---|---|---|---|
| | | | genistin | malonylgenistin | acetylgenistin | genistein |
| pH2.3 | no | 0 | 31.5 | 58.2 | 0.6 | 9.8 |
| | | 1 | not detected | 57.5 | 0.7 | 41.8 |
| | | 3 | not detected | 54.1 | 0.8 | 45.1 |
| | | 6 | not detected | 52.1 | 0.6 | 47.3 |
| | yes | 6 | 35.5 | 54.3 | 0.6 | 9.6 |
| pH3.5 | no | 0 | 31.5 | 58.2 | 0.6 | 9.8 |
| | | 1 | not detected | 27.9 | not detected | 72.1 |
| | | 3 | not detected | 7.5 | not detected | 92.5 |
| | | 6 | not detected | 2.7 | not detected | 97.3 |
| | yes | 6 | 37.0 | 52.7 | 0.5 | 9.8 |
| pH4.8 | no | 0 | 31.7 | 58.6 | 0.5 | 9.1 |
| | | 1 | not detected | 41.0 | not detected | 59.0 |
| | | 3 | not detected | 23.9 | not detected | 76.1 |
| | | 6 | not detected | 11.3 | not detected | 88.7 |
| | yes | 6 | 37.8 | 51.9 | 0.6 | 9.7 |
| pH6.2 | no | 0 | 31.7 | 58.6 | 0.5 | 9.1 |
| | | 1 | not detected | 52.6 | not detected | 47.4 |
| | | 3 | not detected | 41.2 | not detected | 58.8 |
| | | 6 | not detected | 35.8 | not detected | 64.2 |
| | yes | 6 | 38.3 | 51.5 | 0.6 | 9.5 |
| pH7.2 | no | 0 | 31.2 | 57.0 | 0.7 | 11.1 |
| | | 1 | not detected | 56.9 | not detected | 43.1 |
| | | 3 | not detected | 51.5 | not detected | 48.5 |
| | | 6 | not detected | 46.4 | not detected | 53.6 |
| | yes | 6 | 38.9 | 51.1 | 0.7 | 9.3 |
| pH11.6 | no | 0 | 34.8 | 54.2 | 0.5 | 10.5 |
| | | 1 | not detected | 57.7 | not detected | 42.3 |
| | | 3 | not detected | 52.6 | not detected | 47.4 |
| | | 6 | not detected | 49.5 | not detected | 50.5 |
| | yes | 6 | 41.3 | 47.7 | 0.9 | 10.1 |

TABLE 20

Decomposition efficiency of daidzin family in soymilk

| Reaction pH | Heat treatment of enzyme | Reaction time (h) | Glycoside | | | Aglycon |
|---|---|---|---|---|---|---|
| | | | daidzin | malonyldaidzin | acetyldaidzin | daidzein |
| pH2.3 | no | 0 | 34.4 | 55.1 | not detected | 10.5 |
| | | 1 | not detected | 54.7 | not detected | 45.3 |
| | | 3 | not detected | 51.1 | not detected | 48.9 |
| | | 6 | not detected | 48.5 | not detected | 51.5 |
| | yes | 6 | 38.8 | 51.0 | not detected | 10.2 |

TABLE 20-continued

Decomposition efficiency of daidzin family in soymilk

| Reaction pH | Heat treatment of enzyme | Reaction time (h) | Glycoside daidzin | malonyldaidzin | acetyldaidzin | Aglycon daidzein |
|---|---|---|---|---|---|---|
| pH3.5 | no | 0 | 34.4 | 55.1 | not detected | 10.5 |
| | | 1 | not detected | 35.6 | not detected | 64.4 |
| | | 3 | not detected | 15.1 | not detected | 84.9 |
| | | 6 | not detected | 7.4 | not detected | 92.6 |
| | yes | 6 | 40.4 | 49.1 | not detected | 10.6 |
| pH4.8 | no | 0 | 34.9 | 56.2 | not detected | 9.0 |
| | | 1 | not detected | 47.4 | not detected | 52.6 |
| | | 3 | not detected | 33.9 | not detected | 66.1 |
| | | 6 | not detected | 20.3 | not detected | 79.7 |
| | yes | 6 | 41.2 | 49.7 | not detected | 9.1 |
| pH6.2 | no | 0 | 34.9 | 56.2 | not detected | 9.0 |
| | | 1 | not detected | 54.1 | not detected | 45.9 |
| | | 3 | not detected | 46.4 | not detected | 53.6 |
| | | 6 | not detected | 41.9 | not detected | 58.1 |
| | yes | 6 | 40.6 | 49.7 | not detected | 9.7 |
| pH7.2 | no | 0 | 34.9 | 56.1 | not detected | 9.0 |
| | | 1 | not detected | 56.4 | not detected | 43.6 |
| | | 3 | not detected | 52.4 | not detected | 47.6 |
| | | 6 | not detected | 48.2 | not detected | 51.8 |
| | yes | 6 | 41.5 | 48.3 | not detected | 10.2 |
| pH11.6 | no | 0 | 38.8 | 52.5 | not detected | 8.7 |
| | | 1 | not detected | 56.4 | not detected | 43.6 |
| | | 3 | not detected | 50.4 | not detected | 49.6 |
| | | 6 | not detected | 47.7 | not detected | 52.3 |
| | yes | 6 | 44.6 | 46.1 | not detected | 9.3 |

TABLE 21

Decomposition efficiency of glycitin family in concentrated soybean protein

| Reaction pH | Heat treatment of enzyme | Reaction time (h) | Glycoside glycitin | malonylglycitin | acetylglycitin | Aglycon glycitein |
|---|---|---|---|---|---|---|
| pH1.6 | no | 0 | 52.3 | 0.4 | 35.9 | 11.3 |
| | | 1 | 52.9 | 0.4 | 35.1 | 11.6 |
| | | 3 | 54.3 | 0.4 | 33.5 | 11.7 |
| | | 6 | 56.1 | 0.4 | 31.8 | 11.7 |
| | yes | 6 | 57.9 | 0.4 | 30.9 | 10.8 |
| pH2.7 | no | 0 | 52.3 | 0.4 | 35.9 | 11.3 |
| | | 1 | 38.0 | 0.5 | 36.6 | 25.0 |
| | | 3 | 37.2 | 0.5 | 36.5 | 25.7 |
| | | 6 | 33.7 | 0.5 | 36.6 | 29.2 |
| | yes | 6 | 52.7 | 0.4 | 35.4 | 11.5 |
| pH3.7 | no | 0 | 52.4 | 0.4 | 36.1 | 11.1 |
| | | 1 | not detected | 0.5 | 32.9 | 66.7 |
| | | 3 | not detected | 0.4 | 26.1 | 73.5 |
| | | 6 | not detected | 0.4 | 22.1 | 77.5 |
| | yes | 6 | 52.4 | 0.4 | 35.9 | 11.3 |
| pH5.1 | no | 0 | 52.4 | 0.4 | 36.1 | 11.1 |
| | | 1 | 4.1 | 0.6 | 33.2 | 62.1 |
| | | 3 | not detected | 0.6 | 26.0 | 73.4 |
| | | 6 | not detected | 0.6 | 21.0 | 78.5 |
| | yes | 6 | 52.3 | 0.4 | 35.8 | 11.5 |
| pH6.6 | no | 0 | 52.2 | 0.4 | 36.1 | 11.3 |
| | | 1 | 22.6 | 0.4 | 34.8 | 42.2 |
| | | 3 | 6.9 | 0.4 | 32.4 | 60.3 |
| | | 6 | 2.0 | 0.4 | 29.5 | 68.1 |
| | yes | 6 | 53.3 | 0.4 | 35.2 | 11.1 |
| pH8.6 | no | 0 | 54.9 | 0.4 | 33.0 | 11.7 |
| | | 1 | 51.6 | 0.4 | 32.6 | 15.4 |
| | | 3 | 45.9 | 0.4 | 32.6 | 21.0 |
| | | 6 | 36.7 | 0.4 | 32.0 | 30.9 |
| | yes | 6 | 56.8 | 0.3 | 31.6 | 11.3 |

TABLE 22

Decomposition efficiency of genistin family in concentrated soybean protein

| Reaction pH | Heat treatment of enzyme | Reaction time (h) | Glycoside | | | Aglycon |
|---|---|---|---|---|---|---|
| | | | genistin | malonylgenistin | acetylgenistin | genistein |
| pH1.6 | no | 0 | 49.7 | not detected | 42.5 | 7.8 |
| | | 1 | 50.2 | not detected | 42.2 | 7.6 |
| | | 3 | 51.6 | not detected | 40.6 | 7.8 |
| | | 6 | 53.3 | not detected | 38.9 | 7.9 |
| | yes | 6 | 54.4 | not detected | 37.7 | 7.9 |
| pH2.7 | no | 0 | 49.7 | not detected | 42.5 | 7.8 |
| | | 1 | 23.1 | not detected | 44.3 | 32.6 |
| | | 3 | 22.1 | not detected | 43.7 | 34.2 |
| | | 6 | 17.5 | not detected | 44.0 | 38.4 |
| | yes | 6 | 50.5 | not detected | 42.5 | 7.0 |
| pH3.7 | no | 0 | 50.7 | not detected | 43.1 | 6.2 |
| | | 1 | not detected | not detected | 43.5 | 56.5 |
| | | 3 | not detected | not detected | 36.9 | 63.1 |
| | | 6 | not detected | not detected | 30.7 | 69.3 |
| | yes | 6 | 50.6 | not detected | 43.0 | 6.4 |
| pH5.1 | no | 0 | 50.7 | not detected | 43.1 | 6.2 |
| | | 1 | not detected | not detected | 45.2 | 54.8 |
| | | 3 | not detected | not detected | 40.2 | 59.8 |
| | | 6 | not detected | not detected | 35.6 | 64.4 |
| | yes | 6 | 51.4 | not detected | 42.4 | 6.2 |
| pH6.6 | no | 0 | 50.4 | not detected | 43.0 | 6.5 |
| | | 1 | 13.9 | not detected | 43.6 | 42.4 |
| | | 3 | 3.8 | not detected | 42.8 | 53.3 |
| | | 6 | 1.7 | not detected | 41.0 | 57.2 |
| | yes | 6 | 53.2 | not detected | 40.6 | 6.2 |
| pH8.6 | no | 0 | 53.8 | not detected | 39.7 | 6.5 |
| | | 1 | 50.4 | not detected | 38.8 | 10.8 |
| | | 3 | 45.1 | not detected | 39.0 | 15.8 |
| | | 6 | 36.3 | not detected | 38.5 | 25.2 |
| | yes | 6 | 56.2 | not detected | 37.6 | 6.2 |

TABLE 23

Decomposition efficiency of daidzin family in concentrated soybean protein

| Reaction pH | Heat treatment of enzyme | Reaction time (h) | Glycoside | | | Aglycon |
|---|---|---|---|---|---|---|
| | | | daidzin | malonyldaidzin | acetyldaidzin | daidzein |
| pH1.6 | no | 0 | 52.5 | not detected | 44.5 | 3.0 |
| | | 1 | 53.0 | not detected | 43.7 | 3.3 |
| | | 3 | 55.0 | not detected | 41.7 | 3.3 |
| | | 6 | 57.2 | not detected | 39.4 | 3.4 |
| | yes | 6 | 59.0 | not detected | 38.1 | 2.9 |
| pH2.7 | no | 0 | 52.5 | not detected | 44.5 | 3.0 |
| | | 1 | 12.9 | not detected | 46.4 | 40.7 |
| | | 3 | 12.5 | not detected | 46.0 | 41.6 |
| | | 6 | 9.3 | not detected | 45.8 | 45.0 |
| | yes | 6 | 53.0 | not detected | 43.9 | 3.2 |
| pH3.7 | no | 0 | 52.5 | not detected | 44.6 | 3.0 |
| | | 1 | not detected | not detected | 41.6 | 58.4 |
| | | 3 | not detected | not detected | 33.0 | 67.0 |
| | | 6 | not detected | not detected | 25.2 | 74.8 |
| | yes | 6 | 52.5 | not detected | 44.4 | 3.1 |
| pH5.1 | no | 0 | 52.5 | not detected | 44.6 | 3.0 |
| | | 1 | not detected | not detected | 43.4 | 56.6 |
| | | 3 | not detected | not detected | 37.0 | 63.0 |
| | | 6 | not detected | not detected | 31.2 | 68.8 |
| | yes | 6 | 53.4 | not detected | 43.4 | 3.2 |
| pH6.6 | no | 0 | 52.1 | not detected | 44.8 | 3.0 |
| | | 1 | 5.0 | not detected | 43.9 | 51.0 |
| | | 3 | not detected | not detected | 42.9 | 57.1 |
| | | 6 | not detected | not detected | 41.2 | 58.8 |
| | yes | 6 | 55.1 | not detected | 41.8 | 3.2 |

TABLE 23-continued

Decomposition efficiency of daidzin family in concentrated soybean protein

| Reaction pH | Heat treatment of enzyme | Reaction time (h) | Glycoside | | | Aglycon |
|---|---|---|---|---|---|---|
| | | | daidzin | malonyldaidzin | acetyldaidzin | daidzein |
| pH8.6 | no | 0 | 56.1 | not detected | 40.7 | 3.2 |
| | | 1 | 50.8 | not detected | 39.2 | 9.9 |
| | | 3 | 45.0 | not detected | 39.0 | 15.9 |
| | | 6 | 34.5 | not detected | 38.1 | 27.4 |
| | yes | 6 | 59.1 | not detected | 37.7 | 3.2 |

TABLE 24

Decomposition efficiency of glycitin family in defatted soybean

| Reaction pH | Heat treatment of enzyme | Reaction time (h) | Glycoside | | | Aglycon |
|---|---|---|---|---|---|---|
| | | | glycitin | malonylglycitin | acetylglycitin | glycitein |
| pH2.6 | no | 0 | not detected | 100.0 | not detected | not detected |
| | | 1 | not detected | 100.0 | not detected | not detected |
| | | 3 | not detected | 100.0 | not detected | not detected |
| | | 6 | not detected | 100.0 | not detected | not detected |
| | yes | 6 | not detected | 100.0 | not detected | not detected |
| pH3.4 | no | 0 | not detected | 100.0 | not detected | not detected |
| | | 1 | not detected | 100.0 | not detected | not detected |
| | | 3 | not detected | 100.0 | not detected | not detected |
| | | 6 | not detected | 100.0 | not detected | not detected |
| | yes | 6 | not detected | 100.0 | not detected | not detected |
| pH4.8 | no | 0 | not detected | 64.0 | not detected | 36.0 |
| | | 1 | not detected | 40.1 | not detected | 59.9 |
| | | 3 | not detected | 37.5 | not detected | 62.5 |
| | | 6 | not detected | 31.9 | not detected | 68.1 |
| | yes | 6 | not detected | 56.2 | not detected | 43.8 |
| pH5.4 | no | 0 | not detected | 64.0 | not detected | 36.0 |
| | | 1 | not detected | 45.1 | not detected | 54.9 |
| | | 3 | not detected | 100.0 | not detected | not detected |
| | | 6 | not detected | 32.3 | not detected | 67.7 |
| | yes | 6 | not detected | 39.3 | not detected | 60.7 |
| pH6.6 | no | 0 | not detected | 39.6 | not detected | 60.4 |
| | | 1 | not detected | 52.9 | not detected | 47.1 |
| | | 3 | not detected | 53.6 | not detected | 46.4 |
| | | 6 | not detected | 58.1 | not detected | 41.9 |
| | yes | 6 | not detected | 50.3 | not detected | 49.7 |
| pH7.8 | no | 0 | not detected | 66.8 | not detected | 33.2 |
| | | 1 | not detected | 57.5 | not detected | 42.5 |
| | | 3 | not detected | 53.2 | not detected | 46.8 |
| | | 6 | not detected | 49.1 | not detected | 50.9 |
| | yes | 6 | not detected | 55.8 | not detected | 44.2 |

TABLE 25

Decomposition efficiency of genistin family in defatted soybean

| Reaction pH | Heat treatment of enzyme | Reaction time (h) | Glycoside | | | Aglycon |
|---|---|---|---|---|---|---|
| | | | genistin | malonylgenistin | acetylgenistin | genistein |
| pH2.6 | no | 0 | 42.0 | 43.8 | 1.8 | 12.4 |
| | | 1 | 36.3 | 44.4 | 1.7 | 17.7 |
| | | 3 | 20.3 | 45.4 | 1.7 | 32.7 |
| | | 6 | 20.1 | 43.5 | 1.9 | 34.6 |
| | yes | 6 | 44.3 | 42.0 | 1.6 | 12.1 |

TABLE 25-continued

Decomposition efficiency of genistin family in defatted soybean

| Reaction pH | Heat treatment of enzyme | Reaction time (h) | Glycoside | | | Aglycon |
|---|---|---|---|---|---|---|
| | | | genistin | malonylgenistin | acetylgenistin | genistein |
| pH3.4 | no | 0 | 42.0 | 43.8 | 1.8 | 12.4 |
| | | 1 | not detected | 41.6 | 1.5 | 56.9 |
| | | 3 | not detected | 36.4 | 1.1 | 62.5 |
| | | 6 | not detected | 30.4 | 0.8 | 68.8 |
| | yes | 6 | 44.3 | 39.8 | 1.8 | 14.1 |
| pH4.8 | no | 0 | 40.5 | 43.2 | 1.8 | 14.5 |
| | | 1 | not detected | 42.8 | 1.0 | 56.1 |
| | | 3 | not detected | 37.5 | 0.6 | 61.9 |
| | | 6 | not detected | 31.1 | 0.4 | 68.5 |
| | yes | 6 | 31.8 | 41.7 | 1.3 | 25.2 |
| pH5.4 | no | 0 | 40.5 | 43.2 | 1.8 | 14.5 |
| | | 1 | not detected | 48.0 | 0.5 | 51.5 |
| | | 3 | not detected | 44.6 | not detected | 55.4 |
| | | 6 | not detected | 39.7 | not detected | 60.3 |
| | yes | 6 | 6.2 | 45.8 | not detected | 48.0 |
| pH6.6 | no | 0 | 39.2 | 47.1 | 1.7 | 12.0 |
| | | 1 | not detected | 50.1 | 0.6 | 49.3 |
| | | 3 | not detected | 48.3 | 0.3 | 51.4 |
| | | 6 | not detected | 46.1 | 0.2 | 53.7 |
| | yes | 6 | 7.7 | 45.7 | 0.2 | 46.4 |
| pH7.8 | no | 0 | 40.4 | 45.8 | 1.6 | 12.2 |
| | | 1 | 15.7 | 46.6 | 1.0 | 36.7 |
| | | 3 | 12.3 | 44.4 | 0.8 | 42.5 |
| | | 6 | 11.4 | 42.2 | 0.7 | 45.7 |
| | yes | 6 | 37.5 | 39.9 | 0.6 | 22.0 |

TABLE 26

Decomposition efficiency of daidzin family in defatted soybean

| Reaction pH | Heat treatment of enzyme | Reaction time (h) | Glycoside | | | Aglycon |
|---|---|---|---|---|---|---|
| | | | daidzin | malonyldaidzin | acetyldaidzin | daidzein |
| pH2.6 | no | 0 | 45.8 | 41.0 | not detected | 13.2 |
| | | 1 | 37.5 | 41.2 | not detected | 21.3 |
| | | 3 | 17.3 | 41.8 | not detected | 40.9 |
| | | 6 | 16.9 | 40.2 | not detected | 42.9 |
| | yes | 6 | 48.0 | 38.9 | not detected | 13.0 |
| pH3.4 | no | 0 | 45.8 | 41.0 | not detected | 13.2 |
| | | 1 | not detected | 39.4 | not detected | 60.6 |
| | | 3 | not detected | 34.5 | not detected | 65.5 |
| | | 6 | not detected | 29.0 | not detected | 71.0 |
| | yes | 6 | 47.8 | 37.1 | not detected | 15.1 |
| pH4.8 | no | 0 | 43.5 | 40.7 | not detected | 15.7 |
| | | 1 | not detected | 40.5 | not detected | 59.5 |
| | | 3 | not detected | 36.7 | not detected | 63.3 |
| | | 6 | not detected | 30.5 | not detected | 69.5 |
| | yes | 6 | 37.1 | 38.4 | not detected | 24.5 |
| pH5.4 | no | 0 | 43.5 | 40.7 | not detected | 15.7 |
| | | 1 | not detected | 44.2 | not detected | 55.8 |
| | | 3 | not detected | 41.5 | not detected | 58.5 |
| | | 6 | not detected | 36.9 | not detected | 63.1 |
| | yes | 6 | not detected | 44.9 | not detected | 55.1 |
| pH6.6 | no | 0 | 43.6 | 43.1 | not detected | 13.2 |
| | | 1 | not detected | 45.9 | not detected | 54.1 |
| | | 3 | not detected | 44.0 | not detected | 56.0 |
| | | 6 | not detected | 41.8 | not detected | 58.2 |
| | yes | 6 | 9.3 | 41.2 | not detected | 49.5 |

TABLE 26-continued

Decomposition efficiency of daidzin family in defatted soybean

| Reaction pH | Heat treatment of enzyme | Reaction time (h) | Glycoside | | | Aglycon |
|---|---|---|---|---|---|---|
| | | | daidzin | malonyldaidzin | acetyldaidzin | daidzein |
| pH7.8 | no | 0 | 44.7 | 42.0 | not detected | 13.3 |
| | | 1 | 13.3 | 43.6 | not detected | 43.1 |
| | | 3 | 10.1 | 41.4 | not detected | 48.4 |
| | | 6 | 9.4 | 38.7 | not detected | 51.9 |
| | yes | 6 | 41.6 | 36.7 | not detected | 21.7 |

From these results, maximum pH was found to be in the range of 3.5 to 5. Specifically, in the case of roasted soy flour, after the reaction at pH 4 for 6 hours, the existing ratio of aglycon of each isoflavone family was as follows: glycitein 100%, genistein 87%, and daidzein 89%. In the case of soymilk, almost complete decomposition of isoflavone glycosides occurred after the reaction at pH 3.5 for 6 hours, and glycitein was 100%, genistein 97%, and daidzein 93%. In the case of concentrated soybean protein, after the reaction at pH 3.7 for 6 hours, glycitein was 78%, genistein 69%, and daidzein 75%. In the case of defatted soybean, maximum isolation of aglycons was observed after the reaction at pH 3.4 for 6 hours, and glycitein was 68%, genistein 69%, and daidzein 71%.

EXAMPLE 6

Examination of Substrate Concentration in the Conversion into Isoflavone Aglycons by Diglycosidase Using Soybean Materials Into 20 mM acetate buffer of pH 4.0 was suspended 0.1 g, 0.25 g, 0.5 g, 1.0 g, or 1.5 g of each of various soybean materials (roasted soy flour (manufactured by Fuji Shokuryo K.K.), soymilk (manufactured by Gitoh Shokuhin K.K.), defatted soybean (manufactured by Fuji Seiyu K.K.), concentrated soybean protein (manufactured by Fuji Seiyu K.K.)). The pH of the suspension was measured and the liquid volume was adjusted to 4.5 mL while the pH was adjusted to 4.0 with 1N hydrochloric acid. An enzyme solution wherein diglycosidase activity of crude diglycosidase was adjusted to 1.88 AU/mL was added thereto in an amount of 0.5 mL, whereby the final liquid volume was 5.0 mL. Namely, the ratio of the soybean material in the reaction mixture was 2%, 5%, 10%, 20%, or 30% (w/v). The whole was reacted at 55° C. under shaking. To 5 mL of the reaction mixture was added 7 mL of ethanol after 0, 1, 3, and 6 hours of the reaction. After ultrasonication, the mixture was thoroughly mixed. It was subjected to centrifugal separation at 2,000 rpm and room temperature for 5 minutes. Then, 1 μL of the supernatant was placed in a 1.5 mL microtube and was subjected to centrifugal separation at 15,000 rpm and 4° C. for 10 minutes. The supernatant was filtered through a filter and each sample was suitably diluted by a factor of 1 to 6 depending on the substrate concentration. Fifty μL of the diluted solution was analyzed by HLPC (Tables 27 to 38).

TABLE 27

Decomposition efficiency of glycitin family in roasted soy flour

| Substrate concentration (%) | Heat treatment of enzyme | Reaction time (h) | Glycoside | | | Aglycon |
|---|---|---|---|---|---|---|
| | | | glycitin | malonylglycitin | acetylglycitin | glycitein |
| 2 | no | 0 | 50.2 | not detected | 33.6 | 16.2 |
| | | 1 | not detected | not detected | not detected | 100.0 |
| | | 3 | not detected | not detected | not detected | 100.0 |
| | | 6 | not detected | not detected | not detected | 100.0 |
| | yes | 6 | 53.4 | not detected | 34.4 | 12.2 |
| 5 | no | 0 | 54.8 | not detected | 33.8 | 11.4 |
| | | 1 | not detected | not detected | 11.8 | 88.2 |
| | | 3 | not detected | not detected | 7.2 | 92.8 |
| | | 6 | not detected | not detected | not detected | 100.0 |
| | yes | 6 | 54.8 | not detected | 33.8 | 11.4 |
| 10 | no | 0 | 70.3 | not detected | 24.2 | 5.5 |
| | | 1 | not detected | not detected | 16.7 | 83.3 |
| | | 3 | not detected | not detected | 9.7 | 90.3 |
| | | 6 | not detected | not detected | not detected | 100.0 |
| | yes | 6 | 55.0 | not detected | 35.1 | 9.9 |
| 20 | no | 0 | 59.6 | not detected | 31.8 | 8.6 |
| | | 1 | not detected | not detected | 22.9 | 77.1 |
| | | 3 | not detected | not detected | 13.8 | 86.2 |
| | | 6 | not detected | not detected | 10.0 | 90.0 |
| | yes | 6 | 56.0 | not detected | 35.0 | 9.1 |

TABLE 27-continued

Decomposition efficiency of glycitin family in roasted soy flour

| Substrate concentration (%) | Heat treatment of enzyme | Reaction time (h) | Glycoside | | | Aglycon |
|---|---|---|---|---|---|---|
| | | | glycitin | malonylglycitin | acetylglycitin | glycitein |
| 30 | no | 0 | 55.9 | not detected | 35.3 | 8.8 |
| | | 1 | not detected | not detected | 28.4 | 71.6 |
| | | 3 | not detected | not detected | 24.4 | 75.6 |
| | | 6 | not detected | not detected | 13.7 | 86.3 |
| | yes | 6 | 56.9 | not detected | 34.4 | 8.7 |

TABLE 28

Decomposition efficiency of genistin family in roasted soy flour

| Substrate concentration (%) | Heat treatment of enzyme | Reaction time (h) | Glycoside | | | Aglycon |
|---|---|---|---|---|---|---|
| | | | genistin | malonylgenistin | acetylgenistin | genistein |
| 2 | no | 0 | 33.2 | not detected | 44.7 | 22.1 |
| | | 1 | not detected | not detected | 10.6 | 89.4 |
| | | 3 | not detected | not detected | 5.0 | 95.0 |
| | | 6 | not detected | not detected | 1.5 | 98.5 |
| | yes | 6 | 48.4 | not detected | 45.0 | 6.7 |
| 5 | no | 0 | 47.8 | not detected | 44.7 | 7.5 |
| | | 1 | not detected | not detected | 22.1 | 77.9 |
| | | 3 | not detected | not detected | 15.2 | 84.8 |
| | | 6 | not detected | not detected | 9.2 | 90.8 |
| | yes | 6 | 47.8 | not detected | 44.7 | 7.5 |
| 10 | no | 0 | 59.5 | not detected | 38.2 | 2.3 |
| | | 1 | not detected | not detected | 33.3 | 66.7 |
| | | 3 | not detected | not detected | 25.3 | 74.7 |
| | | 6 | not detected | not detected | 18.7 | 81.3 |
| | yes | 6 | 49.5 | not detected | 45.9 | 4.6 |
| 20 | no | 0 | 50.5 | not detected | 46.1 | 3.4 |
| | | 1 | not detected | not detected | 44.1 | 55.9 |
| | | 3 | not detected | not detected | 35.8 | 64.2 |
| | | 6 | not detected | not detected | 28.6 | 71.4 |
| | yes | 6 | 49.5 | not detected | 46.2 | 4.3 |
| 30 | no | 0 | 49.4 | not detected | 46.7 | 3.8 |
| | | 1 | 5.7 | not detected | 46.6 | 47.7 |
| | | 3 | 9.6 | not detected | 41.4 | 48.9 |
| | | 6 | 2.0 | not detected | 37.8 | 60.2 |
| | yes | 6 | 50.1 | not detected | 46.1 | 3.8 |

TABLE 29

Decomposition efficiency of daidzin family in roasted soy flour

| Substrate concentration (%) | Heat treatment of enzyme | Reaction time (h) | Glycoside | | | Aglycon |
|---|---|---|---|---|---|---|
| | | | daidzin | malonyldaidzin | acetyldaidzin | daidzein |
| 2 | no | 0 | 30.2 | not detected | 47.6 | 22.3 |
| | | 1 | not detected | not detected | 9.2 | 90.8 |
| | | 3 | not detected | not detected | not detected | 100.0 |
| | | 6 | not detected | not detected | not detected | 100.0 |
| | yes | 6 | 46.6 | not detected | 47.2 | 6.2 |

TABLE 29-continued

Decomposition efficiency of daidzin family in roasted soy flour

| Substrate concentration (%) | Heat treatment of enzyme | Reaction time (h) | Glycoside | | | Aglycon |
|---|---|---|---|---|---|---|
| | | | daidzin | malonyldaidzin | acetyldaidzin | daidzein |
| 5 | no | 0 | 46.1 | not detected | 46.1 | 7.7 |
| | | 1 | not detected | not detected | 20.9 | 79.1 |
| | | 3 | not detected | not detected | 12.5 | 87.5 |
| | | 6 | not detected | not detected | 6.8 | 93.2 |
| | yes | 6 | 46.1 | not detected | 46.1 | 7.7 |
| 10 | no | 0 | 60.1 | not detected | 38.5 | 1.4 |
| | | 1 | not detected | not detected | 30.5 | 69.5 |
| | | 3 | not detected | not detected | 21.5 | 78.5 |
| | | 6 | not detected | not detected | 14.9 | 85.1 |
| | yes | 6 | 47.5 | not detected | 47.7 | 4.8 |
| 20 | no | 0 | 50.3 | not detected | 46.1 | 3.7 |
| | | 1 | not detected | not detected | 40.7 | 59.3 |
| | | 3 | not detected | not detected | 32.6 | 67.4 |
| | | 6 | not detected | not detected | 25.1 | 74.9 |
| | yes | 6 | 48.6 | not detected | 47.2 | 4.2 |
| 30 | no | 0 | 47.7 | not detected | 47.6 | 4.7 |
| | | 1 | not detected | not detected | 46.4 | 53.6 |
| | | 3 | not detected | not detected | 42.6 | 57.4 |
| | | 6 | not detected | not detected | 34.3 | 65.7 |
| | yes | 6 | 49.0 | not detected | 47.4 | 3.6 |

TABLE 30

Decomposition efficiency of glycitin family in soymilk

| Substrate concentration (%) | Heat treatment of enzyme | Reaction time (h) | Glycoside | | | Aglycon |
|---|---|---|---|---|---|---|
| | | | glycitin | malonylglycitin | acetyl-glycitin | glycitein |
| 2 | no | 0 | 71.8 | 28.2 | not detected | not detected |
| | | 1 | not detected | not detected | not detected | 100.0 |
| | | 3 | not detected | not detected | not detected | 100.0 |
| | | 6 | not detected | not detected | not detected | 100.0 |
| | yes | 6 | 51.8 | 48.2 | not detected | not detected |
| 5 | no | 0 | 49.4 | 50.6 | not detected | not detected |
| | | 1 | not detected | 24.6 | not detected | 75.4 |
| | | 3 | not detected | 7.5 | not detected | 92.5 |
| | | 6 | not detected | not detected | not detected | 100.0 |
| | yes | 6 | 56.7 | 43.3 | not detected | not detected |
| 10 | no | 0 | 52.5 | 41.1 | not detected | 6.4 |
| | | 1 | not detected | 26.4 | not detected | 73.6 |
| | | 3 | not detected | 10.5 | not detected | 89.5 |
| | | 6 | not detected | 4.2 | not detected | 95.8 |
| | yes | 6 | 56.8 | 37.0 | not detected | 6.2 |
| 20 | no | 0 | 52.4 | 41.3 | not detected | 6.3 |
| | | 1 | not detected | 27.8 | not detected | 72.2 |
| | | 3 | not detected | 9.4 | not detected | 90.6 |
| | | 6 | not detected | 5.9 | not detected | 94.1 |
| | yes | 6 | 55.5 | 38.8 | not detected | 5.7 |
| 30 | no | 0 | 50.9 | 43.0 | not detected | 6.1 |
| | | 1 | not detected | 33.1 | not detected | 66.9 |
| | | 3 | not detected | 15.9 | not detected | 84.1 |
| | | 6 | not detected | 7.7 | not detected | 92.3 |
| | yes | 6 | 55.8 | 37.5 | not detected | 6.7 |

TABLE 31

Decomposition efficiency of genistin family in soymilk

| Substrate concentration (%) | Heat treatment of enzyme | Reaction time (h) | Glycoside | | | Aglycon |
|---|---|---|---|---|---|---|
| | | | genistin | malonylgenistin | acetyl-genistin | genistein |
| 2 | no | 0 | 54.5 | 35.0 | not detected | 10.5 |
| | | 1 | not detected | 15.3 | not detected | 84.7 |
| | | 3 | not detected | 3.5 | not detected | 96.5 |
| | | 6 | not detected | 0.0 | not detected | 100.0 |
| | yes | 6 | 38.0 | 49.5 | not detected | 12.5 |
| 5 | no | 0 | 31.5 | 58.2 | not detected | 10.3 |
| | | 1 | not detected | 24.9 | not detected | 75.1 |
| | | 3 | not detected | 6.9 | not detected | 93.1 |
| | | 6 | not detected | 2.1 | not detected | 97.9 |
| | yes | 6 | 37.9 | 52.5 | not detected | 9.7 |
| 10 | no | 0 | 32.9 | 56.5 | 0.5 | 10.1 |
| | | 1 | not detected | 31.5 | not detected | 68.5 |
| | | 3 | not detected | 11.9 | not detected | 88.1 |
| | | 6 | not detected | 4.8 | not detected | 95.2 |
| | yes | 6 | 37.6 | 51.2 | 0.5 | 10.6 |
| 20 | no | 0 | 33.3 | 56.3 | 0.6 | 9.9 |
| | | 1 | not detected | 37.6 | not detected | 62.4 |
| | | 3 | not detected | 15.7 | not detected | 84.3 |
| | | 6 | not detected | 10.7 | not detected | 89.3 |
| | yes | 6 | 38.6 | 51.0 | 0.6 | 9.8 |
| 30 | no | 0 | 33.6 | 55.9 | 0.6 | 9.9 |
| | | 1 | not detected | 42.5 | not detected | 57.5 |
| | | 3 | not detected | 25.4 | not detected | 74.6 |
| | | 6 | not detected | 17.1 | not detected | 82.9 |
| | yes | 6 | 38.6 | 50.0 | 0.6 | 10.9 |

TABLE 32

Decomposition efficiency of daidzin family in soymilk

| Substrate concentration (%) | Heat treatment of enzyme | Reaction time (h) | Glycoside | | | Aglycon |
|---|---|---|---|---|---|---|
| | | | daidzin | malonyldaidzin | acetyl-daidzin | daidzein |
| 2 | no | 0 | 53.5 | 32.2 | not detected | 14.4 |
| | | 1 | not detected | 27.5 | not detected | 72.5 |
| | | 3 | not detected | 9.9 | not detected | 90.1 |
| | | 6 | not detected | 2.9 | not detected | 97.1 |
| | yes | 6 | 39.8 | 47.0 | not detected | 13.1 |
| 5 | no | 0 | 34.2 | 53.6 | not detected | 12.2 |
| | | 1 | not detected | 34.2 | not detected | 65.8 |
| | | 3 | not detected | 15.9 | not detected | 84.1 |
| | | 6 | not detected | 6.1 | not detected | 93.9 |
| | yes | 6 | 40.5 | 47.6 | not detected | 12.0 |
| 10 | no | 0 | 34.6 | 53.4 | not detected | 12.0 |
| | | 1 | not detected | 37.4 | not detected | 62.6 |
| | | 3 | not detected | 20.5 | not detected | 79.5 |
| | | 6 | not detected | 10.7 | not detected | 89.3 |
| | yes | 6 | 39.4 | 47.8 | not detected | 12.8 |
| 20 | no | 0 | 34.1 | 53.6 | not detected | 12.3 |
| | | 1 | not detected | 41.2 | not detected | 58.8 |
| | | 3 | not detected | 21.5 | not detected | 78.5 |
| | | 6 | not detected | 16.4 | not detected | 83.6 |
| | yes | 6 | 39.8 | 48.1 | not detected | 12.1 |
| 30 | no | 0 | 34.9 | 53.5 | not detected | 11.6 |
| | | 1 | not detected | 43.8 | not detected | 56.2 |
| | | 3 | not detected | 29.7 | not detected | 70.3 |
| | | 6 | not detected | 21.9 | not detected | 78.1 |
| | yes | 6 | 40.0 | 46.9 | not detected | 13.1 |

TABLE 33

Decomposition efficiency of glycitin family in concentrated soybean protein

| Substrate concentration (%) | Heat treatment of enzyme | Reaction time (h) | Glycoside | | | Aglycon |
|---|---|---|---|---|---|---|
| | | | glycitin | malonylglycitin | acetylglycitin | glycitein |
| 2 | no | 0 | 52.2 | 0.4 | 35.8 | 11.6 |
| | | 1 | not detected | 0.4 | 14.3 | 85.3 |
| | | 3 | not detected | 0.2 | 5.3 | 94.4 |
| | | 6 | not detected | not detected | 0.0 | 100.0 |
| | yes | 6 | 53.4 | 0.4 | 35.0 | 11.2 |
| 5 | no | 0 | 52.9 | 0.4 | 35.6 | 11.2 |
| | | 1 | not detected | 0.5 | 27.1 | 72.4 |
| | | 3 | not detected | 0.4 | 17.8 | 81.9 |
| | | 6 | not detected | 0.2 | 12.3 | 87.4 |
| | yes | 6 | 54.0 | 0.4 | 34.4 | 11.3 |
| 10 | no | 0 | 52.9 | 0.3 | 35.7 | 11.0 |
| | | 1 | 1.6 | 0.4 | 31.2 | 66.8 |
| | | 3 | not detected | 0.3 | 26.2 | 73.5 |
| | | 6 | not detected | 0.3 | 23.9 | 75.8 |
| | yes | 6 | 53.4 | 0.3 | 35.2 | 11.1 |
| 20 | no | 0 | 53.1 | 0.2 | 35.9 | 10.8 |
| | | 1 | 13.2 | 0.3 | 35.4 | 51.2 |
| | | 3 | not detected | 0.2 | 33.6 | 66.2 |
| | | 6 | not detected | 0.3 | 30.5 | 69.2 |
| | yes | 6 | 52.8 | 0.4 | 35.8 | 11.1 |
| 30 | no | 0 | 57.5 | 0.4 | 33.9 | 8.2 |
| | | 1 | 2.0 | 0.6 | 35.9 | 61.5 |
| | | 3 | not detected | 0.5 | 30.7 | 68.9 |
| | | 6 | not detected | 0.3 | 28.3 | 71.4 |
| | yes | 6 | 58.0 | 0.4 | 33.4 | 8.2 |

TABLE 34

Decomposition efficiency of genistin family in concentrated soybean protein

| Substrate concentration (%) | Heat treatment of enzyme | Reaction time (h) | Glycoside | | | Aglycon |
|---|---|---|---|---|---|---|
| | | | genistin | malonylgenistin | acetylgenistin | genistein |
| 2 | no | 0 | 50.5 | not detected | 42.9 | 6.6 |
| | | 1 | 1.2 | not detected | 20.0 | 78.7 |
| | | 3 | not detected | not detected | 8.3 | 91.7 |
| | | 6 | not detected | not detected | 3.3 | 96.7 |
| | yes | 6 | 51.6 | not detected | 41.3 | 7.0 |
| 5 | no | 0 | 51.2 | not detected | 43.1 | 5.8 |
| | | 1 | not detected | not detected | 36.4 | 63.6 |
| | | 3 | not detected | not detected | 26.3 | 73.7 |
| | | 6 | not detected | not detected | 17.8 | 82.2 |
| | yes | 6 | 52.2 | not detected | 41.7 | 6.2 |
| 10 | no | 0 | 50.6 | not detected | 43.4 | 5.9 |
| | | 1 | 1.3 | not detected | 42.8 | 55.8 |
| | | 3 | not detected | not detected | 37.3 | 62.7 |
| | | 6 | not detected | not detected | 33.2 | 66.8 |
| | yes | 6 | 50.9 | not detected | 42.8 | 6.3 |
| 20 | no | 0 | 50.4 | not detected | 43.7 | 5.9 |
| | | 1 | 6.0 | not detected | 47.0 | 46.9 |
| | | 3 | not detected | not detected | 44.6 | 55.4 |
| | | 6 | not detected | not detected | 42.3 | 57.7 |
| | yes | 6 | 50.8 | not detected | 43.2 | 6.1 |
| 30 | no | 0 | 54.6 | not detected | 43.5 | 1.9 |
| | | 1 | 2.8 | not detected | 65.3 | 31.9 |
| | | 3 | not detected | not detected | 61.0 | 39.0 |
| | | 6 | not detected | not detected | 55.9 | 44.1 |
| | yes | 6 | 55.6 | not detected | 42.4 | 2.0 |

TABLE 35

Decomposition efficiency of daidzin family in concentrated soybean protein

| Substrate concentration (%) | Heat treatment of enzyme | Reaction time (h) | Glycoside diadzin | Glycoside malonydaidzin | Glycoside acetly-daidzin | Aglycon daidzein |
|---|---|---|---|---|---|---|
| 2 | no | 0 | 52.8 | not detected | 44.0 | 3.2 |
| | | 1 | not detected | not detected | 17.8 | 82.2 |
| | | 3 | not detected | not detected | 5.3 | 94.7 |
| | | 6 | not detected | not detected | not detected | 100.0 |
| | yes | 6 | 52.6 | not detected | 43.2 | 4.2 |
| 5 | no | 0 | 53.0 | not detected | 44.0 | 3.1 |
| | | 1 | not detected | not detected | 32.6 | 67.4 |
| | | 3 | not detected | not detected | 20.5 | 79.5 |
| | | 6 | not detected | not detected | 12.0 | 88.0 |
| | yes | 6 | 53.5 | not detected | 43.0 | 3.5 |
| 10 | no | 0 | 52.8 | not detected | 44.2 | 3.0 |
| | | 1 | 2.2 | not detected | 39.7 | 58.1 |
| | | 3 | not detected | not detected | 32.9 | 67.1 |
| | | 6 | not detected | not detected | 26.9 | 73.1 |
| | yes | 6 | 53.3 | not detected | 43.4 | 3.3 |
| 20 | no | 0 | 52.9 | not detected | 44.1 | 3.0 |
| | | 1 | 0.7 | not detected | 46.4 | 52.9 |
| | | 3 | not detected | not detected | 41.5 | 58.5 |
| | | 6 | not detected | not detected | 37.9 | 62.1 |
| | yes | 6 | 52.8 | not detected | 44.0 | 3.2 |
| 30 | no | 0 | 49.2 | not detected | 49.2 | 1.7 |
| | | 1 | 2.7 | not detected | 56.6 | 40.7 |
| | | 3 | not detected | not detected | 49.9 | 50.1 |
| | | 6 | not detected | not detected | 42.8 | 57.2 |
| | yes | 6 | 49.8 | not detected | 48.4 | 1.8 |

TABLE 36

Decomposition efficiency of glycitin family in defatted soybean

| Substrate concentration (%) | Heat treatment of enzyme | Reaction time (h) | Glycoside glycitin | Glycoside malonylglycitin | Glycoside acetylglycitin | Aglycon glycitein |
|---|---|---|---|---|---|---|
| 2 | no | 0 | not detected | not detected | not detected | not detected |
| | | 1 | not detected | not detected | not detected | not detected |
| | | 3 | not detected | not detected | not detected | not detected |
| | | 6 | not detected | not detected | not detected | not detected |
| | yes | 6 | not detected | not detected | not detected | not detected |
| 5 | no | 0 | not detected | 58.4 | not detected | 41.6 |
| | | 1 | not detected | 41.6 | not detected | 58.4 |
| | | 3 | not detected | 31.8 | not detected | 68.2 |
| | | 6 | not detected | 19.5 | not detected | 80.5 |
| | yes | 6 | not detected | 58.5 | not detected | 41.5 |
| 10 | no | 0 | not detected | 53.0 | not detected | 47.0 |
| | | 1 | not detected | 54.7 | not detected | 45.3 |
| | | 3 | not detected | 36.6 | not detected | 63.4 |
| | | 6 | not detected | 27.9 | not detected | 72.1 |
| | yes | 6 | not detected | 57.6 | not detected | 42.4 |

TABLE 37

Decomposition efficiency of genistin family in defatted soybean

| Substrate concentration (%) | Heat treatment of enzyme | Reaction time (h) | Glycoside genisitin | Glycoside malonylgenistin | Glycoside acetylgenistin | Aglycon genistein |
|---|---|---|---|---|---|---|
| 2 | no | 0 | 37.7 | 45.4 | 1.8 | 15.1 |
| | | 1 | not detected | 31.4 | not detected | 68.6 |
| | | 3 | not detected | 17.0 | not detected | 83.0 |
| | | 6 | not detected | 11.4 | not detected | 88.6 |
| | yes | 6 | 38.7 | 41.8 | 1.5 | 18.0 |

TABLE 37-continued

Decomposition efficiency of genistin family in defatted soybean

| Substrate concentration (%) | Heat treatment of enzyme | Reaction time (h) | Glycoside genisitin | malonylgenistin | acetylgenistin | Aglycon genistein |
|---|---|---|---|---|---|---|
| 5 | no | 0 | 40.0 | 43.9 | 1.9 | 14.2 |
|  |  | 1 | not detected | 38.0 | 0.8 | 61.2 |
|  |  | 3 | not detected | 29.6 | 0.5 | 69.9 |
|  |  | 6 | not detected | 19.0 | 0.3 | 80.7 |
|  | yes | 6 | 41.8 | 41.1 | 1.8 | 15.4 |
| 10 | no | 0 | 42.4 | 41.6 | 1.9 | 14.1 |
|  |  | 1 | not detected | 41.5 | 1.3 | 57.2 |
|  |  | 3 | not detected | 35.1 | 0.9 | 64.0 |
|  |  | 6 | not detected | 29.1 | 0.6 | 70.3 |
|  | yes | 6 | 44.3 | 39.4 | 1.7 | 14.5 |

TABLE 38

Decomposition efficiency of daidzin family in defatted soybean

| Substrate concentration (%) | Heat treatment of enzyme | Reaction time (h) | Glycoside daidzin | malonyldaidzin | acetyldaidzin | Aglycon daidzein |
|---|---|---|---|---|---|---|
| 2 | no | 0 | 42.3 | 42.2 | not detected | 15.5 |
|  |  | 1 | not detected | 35.2 | not detected | 64.8 |
|  |  | 3 | not detected | 21.2 | not detected | 78.8 |
|  |  | 6 | not detected | 16.5 | not detected | 83.5 |
|  | yes | 6 | 43.7 | 38.1 | not detected | 18.2 |
| 5 | no | 0 | 44.0 | 41.1 | not detected | 14.9 |
|  |  | 1 | not detected | 37.7 | not detected | 62.3 |
|  |  | 3 | not detected | 30.6 | not detected | 69.4 |
|  |  | 6 | not detected | 21.0 | not detected | 79.0 |
|  | yes | 6 | 45.8 | 38.1 | not detected | 16.1 |
| 10 | no | 0 | 45.6 | 39.7 | not detected | 14.7 |
|  |  | 1 | not detected | 39.5 | not detected | 60.5 |
|  |  | 3 | not detected | 34.2 | not detected | 65.8 |
|  |  | 6 | not detected | 29.0 | not detected | 71.0 |
|  | yes | 6 | 47.5 | 37.0 | not detected | 15.5 |

By combining maximum reaction temperature and pH, in all the materials examined, isolation of each isoflavone glucoside was found to be 70% or more when the material concentration is 10% or less. In particular, when the material concentration ranges from 2% to 5%, it was revealed that almost 100% conversion of isoflavone glycosides into aglycons occurred.

EXAMPLE 7

Influence of Commercially Available Enzyme Preparations Accelerating the Conversion into Aglycon Isoflavones by Diglycosidase Soyaflavone (manufactured by Fuji Seiyu K.K.) was suspended into 1.0 M sodium acetate of pH 3.0 and the substrate concentration was adjusted to 30% (w/v) and pH of the solution to 5.0. The suspension was pre-incubated at 50° C. for 1 hour, whereby the temperature of the suspension was elevated to 50° C. To the suspension was added each commercially available enzyme preparation (Amylase AD "Amano" 1, YL-15, Gluczyme NL4.2, Transglucosidase L "Amano", all manufactured by Amano Enzyme Inc.) solely or in combination with diglycosidase (0.3 AU) so as to be 0.1% (w/v). The whole was reacted at 50° C. for 6 hours and the change of the composition of isoflavone glycosides and aglycon isoflavones was analyzed by HPLC. Isoflavone glycosides and aglycon isoflavones were quantitatively determined. Among them, relative values of the aglycon isoflavones were shown in FIG. 1, ideal values of the aglycon isoflavones being 100%.

The ideal value of each aglycon isoflavone was calculated as follows based on the content of each isoflavone glycoside and aglycon isoflavone in the case that no enzyme was added.

Ideal value of aglycon isoflavone=$AG+G1 \times M_{AG}/M_{G1}+G2 \times M_{AG}/M_{G2}+ \ldots$ AG; amount of aglycon isoflavone, G1; amount of isoflavone glycoside, $M_{AG}$; molecular weight of aglycon isoflavone, $M_G$; molecular weight of isoflavone glycoside Each commercially available enzyme preparation it self could hardly hydrolyze glycosides but the combination with diglycosidase obviously increased the amount of isolated aglycon isoflavones. For example, the combination of diglycosidase with Amylase AD "Amano" 1 resulted in 2.1-fold increase of glycitein and 1.3-fold increase of genistein as compared with the action of diglycosidase alone. However, about 1.1-fold increase was observed for daidzein. It was revealed that the combination of diglycosidase with YL-15 resulted in 1.8-fold increase of glycitein, 1.2-fold increase of genistein, and 1.1-fold increase of daidzein, the combination of diglycosidase with Gluczyme NL-4.2 resulted in 0.8-fold increase of glycitein, 1.1-fold increase of genistein, and 1.0-fold increase of daidzein, and the combination of diglycosidase with Transglucosidase L "Amano" resulted in 1.6-fold increase of glycitein, 1.0-fold increase of genistein, and 1.0-fold increase of daidzein.

EXAMPLE 8

Examination of Effective Amount of Amylase AD "Amano" 1 Accelerating the Conversion into Aglycon Isoflavones by Diglycosidase Roasted soy flour (manufactured by Fuji Shokuhin K.K.) was suspended into 0.1 M sodium acetate adjusted to pH 3.15, the substrate concentration was adjusted to 30% (w/v), and the pH of the solution to 5.0. The suspension was pre-incubated at 50° C. for 1 hour, whereby the temperature of the suspension was elevated to 50° C. To the suspension were added diglycosidase so as to be a final concentration of 0.1% (w/v) (0.3 AU) and Amylase AD "Amano" 1 (manufactured by Amano Enzyme Innc.) so as to be 0.1, 0.05, 0.01, 0.005, and 0.0001% (w/v). The whole was reacted at 50° C. for 3 hours and the change of isoflavone composition was analyzed by HPLC.

Figure 2:
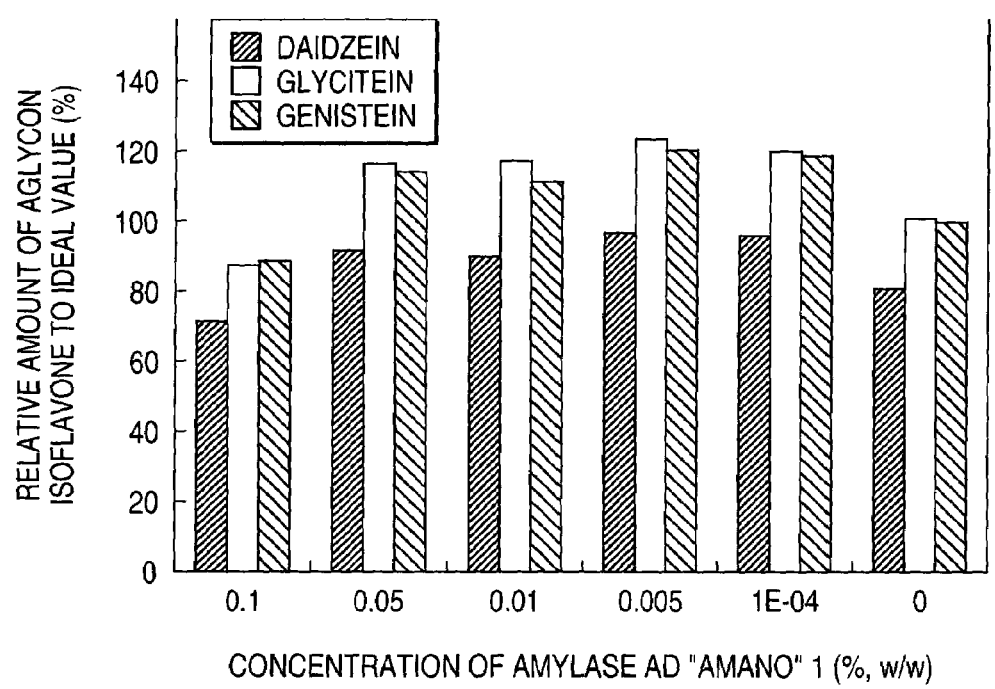
FIG. 2 is a graph showing the results of Example 8.

As shown in FIG. 2, it is found that the isolated amount of aglycon rather increased at a concentration lower than 0.1% (w/v). An effect was observed even at a mall amount of 0.0001% (w/v). At 0.005% (w/v), glycitein and genistein increased by a factor of 1.23 and 1.20, respectively. In the case of daidzein, 1.2-fold increase was observed. By the way, 0% means the results in the case of diglycosidase alone.

EXAMPLE 9

Flavor Improvement of Soybean Protein by Diglycosidase or Each Commercially Available Enzyme Preparation To 10 g of Fujipro (separated soybean protein, manufactured by Fuji Seiyu K.K.) was added 90 mL of water, and the whole was thoroughly mixed to obtain a soybean protein solution. Thereto was added diglycosidase or each of commercially available enzyme preparation (Amylase AD "Amano" 1, ADG-S-DS, Lipase A "Amano" 6, Lactase F-DS, Lactase F, Cellulase A "Amano" 3, Hemicellulase "Amano" 90G, Protease B, YL-15, Pectinase PL "Amano", Transglucosidase L "Amano", Gluczyme NL4.2, all manufactured by Amano Enzyme Inc.) so that diglycosidase (0.5 AU) or each enzyme preparation was contained in the soybean protein solution in a concentration of 0.25% (w/v). The treatment was carried out at 50° C. for 5 hours. By the way, the reaction pH was 7.1. For a sensory test, pH was not adjusted for avoiding the influence of a buffer (the same shall apply to Examples 10 to 12).

Sensory Test (Flavor Improvement of Separated Soybean Protein Treated with Diglycosidase or Each Commercially Available Enzyme Preparation)

For carrying out a sensory test, each soybean protein treated with diglycosidase or each commercially available enzyme preparation was subjected to centrifugal separation at 1500×g and 4° C. for 20 minutes. The precipitate was removed and pH of the supernatant was adjusted to 6.0 with hydrochloric acid. Using a solution obtained by two-fold dilution of the solution, the test was carried out. The evaluation was conducted by five expert panelists, and the deliciousness, bitterness·astringency, and aftertaste were compared with those of Control untreated with the enzyme (Table 39).

TABLE 39

Flavor-improving effect of enzyme preparation on separated soybean protein

| Enzyme name | Panelist A | | | Panelist B | | | Panelist C | | |
|---|---|---|---|---|---|---|---|---|---|
| | deliciousness | bitterness · astringency | aftertaste | deliciousness | bitterness · astringency | aftertaste | deliciousness | bitterness · astringency | aftertaste |
| Untreated (Control) | ± | ± | ± | ± | ± | ± | ± | ± | ± |
| Diglycosidase | ± | -- | + | ± | - | + | ± | -- | ± |
| Amylase AD "Amano" 1 | ± | -- | + | ± | -- | ± | ± | - | ± |
| ADG-D-DS | ± | -- | + | ± | - | ± | ± | - | ++ |
| Lipase A "Amano" 6 | ± | ± | + | ± | - | + | ± | ± | + |
| Lactase F-DS | ± | ± | ± | ± | ± | - | ± | ± | ± |
| Lactase F "Amano" | ± | ± | ± | ± | ± | ± | ± | ± | ± |
| Cellulase A "Amano" 3 | ± | -- | + | ± | -- | ± | ± | - | ± |
| Hemicellulase "Amano" 90G | ± | -- | + | ± | -- | ± | ± | - | ± |
| Protease B | ± | + | ± | ± | ± | ± | ± | ± | ± |
| YL-15 | ± | +++ | + | ± | +++ | ± | ± | +++ | ± |
| Pectinase PL | ± | ± | + | ± | ± | ± | ± | ± | ± |
| Trans- glucosidase L | ± | ± | ± | ± | ± | ± | ± | ± | ± |
| Gluczyme | ± | ± | ± | ± | ± | ± | ± | ± | ± |

TABLE 39-continued

|  | Panelist D | | | Panelist E | | |
|---|---|---|---|---|---|---|
| Enzyme name | deliciousness | bitterness · astringency | aftertaste | deliciousness | bitterness · astringency | aftertaste |
| Untreated (Control) | ± | ± | ± | ± | ± | ± |
| Diglycosidase | + | ± | + | + | − | ± |
| Amylase AD "Amano" 1 | ± | ± | ± | ± | − | ± |
| ADG-D-DS | + | ± | + | ± | − | ± |
| Lipase A "Amano" 6 | ± | ± | + | ± | ± | ± |
| Lactase F-DS | ± | ± | − | ± | ± | ± |
| Lactase F "Amano" | ± | ± | ± | ± | ± | ± |
| Cellulase A "Amano" 3 | + | − | ± | + | −− | ± |
| Hemicellulase "Amano" 90G | ± | − | ± | ± | ± | + |
| Protease B | ± | ± | ± | ± | ± | ± |
| YL-15 | ± | +++ | ± | ± | + | ± |
| Pectinase PL | ± | ± | ± | ± | ± | ± |
| Transglucosidase L | ± | ± | ± | ± | ± | ± |
| Gluczyme | ± | ± | ± | ± | ± | ± |

±; No change is observed as compared with Control.
+; This means that "deliciousness" and "aftertaste" are improved and "bitterness·astringency" is strengthened.
−; This means that "deliciousness" and "aftertaste" become worse and "bitterness·astringency" is reduced.
The increase in number of + and − means that the tendency becomes strong.

As a result, the bitterness-astringency was reduced or disappeared by diglycosidase, Amylase AD "Amano" 1, ADG-S-DS, Lipase A "Amano" 6, Cellulase A "Amano" 3, or Hemicellulase "Amano" 90G.

Also, it was revealed that the treatment with diglycosidase, Amylase AD "Amano" 1, ADG-S-DS, Lipase A "Amano" 6, Cellulase A "Amano" 3, Hemicellulase "Amano" 90G, YL-15, or Pectinase PL "Amano" was effective for improving aftertaste. It was revealed that these enzyme preparations improve overall flavor, for example, appearance of sweetness and reduction of smelling of grass, other than the examined articles.

EXAMPLE 10

Flavor Improvement of Soybean Protein by Diglycosidase and Each Commercially Available Enzyme Preparation To 10 g of Fujipro (separated soybean protein, manufactured by Fuji Seiyu K.K.) was added 90 mL of water, and the whole was thoroughly mixed to obtain a soybean protein solution. Thereto was added diglycosidase and each of commercially available enzyme preparation (Amylase AD "Amano" 1, ADG-S-DS, Lipase A "Amano" 6, Lactase F-DS, Lactase F, Cellulase A "Amano" 3, Hemicellulase "Amano" 90G, Protease B, YL-15, Pectinase PL "Amano", Transglucosidase L "Amano", Gluczyme NL4.2, all manufactured by Amano Enzyme Inc.) so that diglycosidase was contained 6.5 AU in the soybean protein solution and each enzyme preparation in a concentration of 0.25% (w/v). The treatment was carried out at 50° C. for 5 hours to obtain an enzyme-treated soybean protein. By the way, the reaction pH was 7.1.

Sensory Test (Flavor Improvement of Separated Soybean Protein Treated with Diglycosidase and Each Commercially Available Enzyme Preparation)

For carrying out a sensory test, each soybean protein treated with enzymes was subjected to centrifugal separation at 1500×g and 4° C. for 20 minutes. The precipitate was removed and pH of the supernatant was adjusted to 6.0 with hydrochloric acid. Using a solution obtained by two-fold dilution of the solution, the test was carried out. The evaluation was conducted by five expert panelists, and the deliciousness, bitterness·astringency, and aftertaste were compared with those of Control untreated with the enzyme (Table 40).

TABLE 40

Flavor improvement of separated soybean protein by combination of enzymes

|  | Panelist A | | | Panelist B | | | Panelist C | | |
|---|---|---|---|---|---|---|---|---|---|
| Enzyme name | deliciousness | bitterness · astringency | aftertaste | deliciousness | bitterness · astringency | aftertaste | deliciousness | bitterness · astringency | aftertaste |
| Untreated (Control) | ± | ± | ± | ± | ± | ± | ± | ± | ± |
| Diglycosidase + Amylase AD "Amano" 1 | ± | −−− | + | + | −−− | + | ± | −− | ± |
| Diglycosidase + ADG-S-DS | + | −−− | ± | + | − | ± | ++ | −− | ++ |
| Diglycosidase + Lipase A "Amano"6 | + | −−− | ± | ± | − | ± | + | ± | + |
| Diglycosidase + Lactase F-DS | ± | − | ± | ± | − | ± | + | ± | ± |
| Diglycosidase + Lactase F "Amano" | ± | ± | + | + | − | ± | + | ± | + |

TABLE 40-continued

| Enzyme name | | | | | | | | | |
|---|---|---|---|---|---|---|---|---|---|
| Diglycosidase + Cellulase A "Amano"3 | ± | --- | ++ | + | --- | + | + | − | ± |
| Diglycosidase + Hemicellulase "Amano"90G | ± | --- | ++ | + | -- | ± | + | − | ± |
| Diglycosidase + Protease B | ± | --- | ± | + | − | ± | ± | -- | ± |
| Diglycosidase + YL-15 | ± | + | + | + | + | + | + | ± | + |
| Diglycosidase + Pectinase PL "Amano" | ± | − | ++ | + | − | ± | + | -- | ± |
| Diglycosidase + Transglucosidase L "Amano" | ± | − | ± | ± | − | ± | ± | − | ± |
| Diglycosidase + Gluczyme NL4.2 | ± | ± | ± | + | − | ± | ± | ± | ± |

| | Panelist D | | | Panelist E | | |
|---|---|---|---|---|---|---|
| Enzyme name | deliciousness | bitterness · astringency | aftertaste | deliciousness | bitterness · astringency | aftertaste |
| Untreated (Control) | ± | ± | ± | ± | ± | ± |
| Diglycosidase + Amylase AD "Amano"1 | ++ | ± | ± | + | -- | ++ |
| Diglycosidase + ADG-S-DS | ++ | − | ++ | ± | -- | + |
| Diglycosidase + Lipase A "Amano"6 | ++ | ± | + | ± | − | + |
| Diglycosidase + Lactase F-DS | ± | ± | ± | + | − | ± |
| Diglycosidase + Lactase F "Amano" | + | ± | + | ± | -- | ++ |
| Diglycosidase + Cellulase A "Amano"3 | ++ | − | ± | + | --- | + |
| Diglycosidase + Hemicellulase "Amano" 90G | ++ | − | ++ | + | − | ± |
| Diglycosidase + Protease B | ++ | ± | ± | ± | − | + |
| Diglycosidase + YL-15 | + | ++ | + | ± | ± | + |
| Diglycosidase + Pectinase PL "Amano" | ++ | ± | + | ± | − | + |
| Diglycosidase + Transglucosidase L "Amano" | + | ± | ± | + | − | ± |
| Diglycosidase + Gluczyme NL4.2 | + | ± | ± | ± | − | ± |

As a result, it was revealed that effects, for example, appearance of sweetness, reduction of bitterness·astringency, or improvement of aftertaste were observed in all the combinations of diglycosidase and each commercially available enzyme preparation (diglycosidase and Amylase AD "Amano" 1, diglycosidase and ADG-S-DS, diglycosidase and Lipase A "Amano" 6, diglycosidase and Lactase F-DS, diglycosidase and Lactase F "Amano", diglycosidase and Cellulase A "Amano" 3, diglycosidase and Hemicellulase "Amano" 90G, diglycosidase and Protease B, diglycosidase and YL-15, diglycosidase and Pectinase PL "Amano", diglycosidase and Transglucosidase L "Amano", diglycosidase and Gluczyme NL4.2) shown in the table. From these facts, it was evident that flavor-improving effect was stronger in the combination of diglycosidase and each commercially available enzyme preparation than in the case of diglycosidase alone.

EXAMPLE 11

Flavor Improvement of Soymilk by Diglycosidase or Each Commercially Available Enzyme Preparation To 20 mL of an ingredient-unadjusted soymilk (Gitoh Shokuhin K.K.) was added diglycosidase or each of commercially available enzyme preparation (ADG-S-DS, Amylase AD "Amano" 1, Cellulase A "Amano" 3, Hemicellulase "Amano" 90G, all manufactured by Amano Enzyme Inc.) so that diglycosidase was contained 6.5 AU in the soymilk or each enzyme preparation in a concentration of 0.25% (w/v). The treatment was carried out at 55° C. for 1.5 hours. Thereafter, the enzymes were inactivated by heat treatment at 70° C. for 1 hour. By the way, the reaction pH was 6.6.

Sensory Test (Flavor Improvement of Soymilk Treated with Diglycosidase or Each Commercially Available Enzyme Preparation)

The enzyme-treated liquid thus obtained was diluted with water by a factor of 3, and then subjected to a sensory test. The evaluation was conducted by five expert panelists, and the deliciousness, bitterness astringency, and aftertaste were compared with those of Control untreated with the enzyme (Table 41).

TABLE 41

Flavor-improving effect of enzyme preparation on soymilk

| Enzyme name | Panelist A | | | Panelist B | | | Panelist C | | |
|---|---|---|---|---|---|---|---|---|---|
| | sweet-ness | bitter-ness* astrin-gency | after-taste | sweet-ness | bitter-ness* astrin-gency | after-taste | sweet-ness | bitter-ness* astrin-gency | after-taste |
| Untreated (Control) | ± | ± | ± | ± | ± | ± | ± | ± | ± |
| Diglycosidase | ± | − | ± | ± | ± | ± | + + | − | + |
| ADG-D-DS | + | − | ± | + | − | + | ± | − | ± |
| Amylase AD "Amano" 1 | + | − − | + | + | − | + | + | − | ± |
| Cellulase A "Amano" 3 | ± | ± | ± | + | − | + | ± | − | ± |
| Hemicellulase "Amano" 90G | ± | ± | ± | + | − | + | ± | ± | ± |

| Enzyme name | Panelist D | | | Panelist E | | |
|---|---|---|---|---|---|---|
| | sweet-ness | bitter-ness* astrin-gency | after-taste | sweet-ness | bitter-ness* astrin-gency | after-taste |
| Untreated (Control) | ± | ± | ± | ± | ± | ± |
| Diglycosidase | + | ± | ± | + | ± | ± |
| ADG-D-DS | + | ± | ± | + | ± | ± |
| Amylase AD "Amano" 1 | ± | ± | ± | ± | ± | ± |
| Cellulase A "Amano" 3 | ± | ± | ± | + | − | + |
| Hemicellulase "Amano" 90G | ± | ± | ± | + | − | + |

It was revealed that appearance of sweetness, reduction of bitterness·astringency, and improvement of aftertaste were effected by diglycosidase or a commercially available enzyme preparation.

EXAMPLE 12

Flavor Improvement of Soymilk by Diglycosidase and Each Commercially Available Enzyme Preparation To 20 mL of an ingredient-unadjusted soymilk (Gitoh Shokuhin K.K.) was added diglycosidase and each of commercially available enzyme preparation (ADG-S-DS, Amylase AD "Amano" 1, Cellulase A "Amano" 3, or Hemicellulase "Amano" 90G, all manufactured by Amano Enzyme Inc.) so that diglycosidase was contained 6.5 AU in the soymilk and each enzyme preparation in a concentration of 0.25% (w/v). The treatment was carried out at 55° C. for 1.5 hours. Thereafter, the enzymes were inactivated by heat treatment at 70° C. for 1 hour. By the way, the reaction pH was 6.6.

Sensory Test (Flavor Improvement of Soymilk Treated with Diglycosidase and Each Commercially Available Enzyme Preparation)

The enzyme-treated liquid thus obtained was -diluted with water by a factor of 3, and then subjected to a sensory test. The evaluation was conducted by five expert panelists, and the deliciousness, bitterness·astringency, and aftertaste were compared with those of Control untreated with the enzyme (Table 42).

TABLE 42

Flavor improvement of soymilk by combination of enzymes

| Enzyme name | Panelist A | | | Panelist B | | | Panelist C | | |
|---|---|---|---|---|---|---|---|---|---|
| | sweet-ness | bitter-ness* astrin-gency | after-taste | sweet-ness | bitter-ness* astrin-gency | after-taste | sweet-ness | bitter-ness* astrin-gency | after-taste |
| Untreated (Control) | ± | ± | ± | ± | ± | ± | ± | ± | ± |
| Diglycosidase + ADG-S-DS | + | − − | ± | + | − | + | + + | − − | + |

TABLE 42-continued

Flavor improvement of soymilk by combination of enzymes

| | | | | | | | | | |
|---|---|---|---|---|---|---|---|---|---|
| Diglycosidase + Amylase AD "Amano" 1 | + | - - - | + | + | - - | ± | + | - - | ± |
| Diglycosidase + Cellulase A "Amano" 3 | ± | - | ± | + | - | + + | + + | - - | + |
| Diglycosidase + Hemicellulase "Amano" 90G | + | - | ± | + | - | + | + | - | ± |

| | Panelist D | | | Panelist E | | |
|---|---|---|---|---|---|---|
| Enzyme name | sweetness | bitterness* astringency | aftertaste | sweetness | bitterness* astringency | aftertaste |
| Untreated (Control) | ± | ± | ± | ± | ± | ± |
| Diglycosidase + ADG-S-DS | + | - | ± | + + | ± | ± |
| Diglycosidase + Amylase AD "Amano" 1 | + | - | + | + | ± | ± |
| Diglycosidase + Cellulase A "Amano" 3 | + | - | + | + + | - | + |
| Diglycosidase + Hemicellulase "Amano" 90G | + | ± | ± | + + | - | + |

As a result of the sensory test, it was revealed that effects, for example, appearance of sweetness, reduction of bitterness·astringency, or improvement of aftertaste were observed in all the combinations of diglycosidase and each commercially available enzyme preparation (diglycosidase and ADG-S-DS, diglycosidase and Amylase AD "Amano" 1, diglycosidase and Cellulase A "Amano" 3, diglycosidase and Hemicellulase "Amano" 90G) shown in the table. Furthermore, it was revealed that such a treatment with the enzymes improves overall flavor, for example, reduction of smelling of grass. From these facts, it was evident that flavor-improving effect was stronger in the combination of diglycosidase and each commercially available enzyme preparation than in the case of diglycosidase alone or a commercially available enzyme preparation alone.

EXAMPLE 13

Formation of Aglycon Isoflavones from Defatted Soybean Protein by Diglycosidase at the pH in a Stomach Into 20 mM acetate buffer of pH 4.0 was suspended 0.05 g of defatted soybean protein (Fuji Seiyu K.K.). The pH of the suspension was measured and the liquid volume was adjusted to 4.5 mL while the pH was adjusted to 4.0 with 1N hydrochloric acid. An enzyme solution wherein the diglycosidase activity of crude diglycosidase was adjusted to 1.88 AU/mL was added thereto in an amount of 0.5 mL, whereby the final liquid volume was 5.0 mL (concentration of defatted soybean protein: 1% (w/v)), followed by treatment at 37° C. for 3 hours. After the treatment, 75 µL of methanol and 500 µL of water were added to 25 µL of the reaction mixture. The whole was filtered through a 0.2 µm filter and then the filtrate was further diluted with water by a factor of 2.5, followed by HPLC analysis.

As a result of treating defatted soybean protein at pH 4 which was the pH range in a stomach during a meal as described above, no isolation of aglycon isoflavones was observed in the treatment at pH 4 without adding the enzyme, but isolation of aglycon isoflavones was observed in the product treated with diglycosidase. Therefore, it was proved that diglycosidase could convert isoflavone glycosides into aglycon isoflavones under the pH condition in a stomach.

EXAMPLE 14

Formation of Aglycon Isoflavones from Roasterd Soy Flour by Diglycosidase at the pH in a Stomach Into 100 mL of 50 mM acetate buffer (pH 5) was suspended 2.5 g of roasted soy flour (manufactured by Kakudai Sangyo).

To 3 mL of the suspension was added 0.001, 0.002, 0.005, 0.01, 0.025, 0.05, 0.075, 0.15, 0.374, 0.75, or 1.5 mg of diglycosidase (290 AU/g), followed by incubation under shaking at 37° C. for 30 minutes. After the reaction, 10 mL of methanol was added thereto, and aglycon isoflavones were extracted and analyzed by HPLC.

Figure 3:
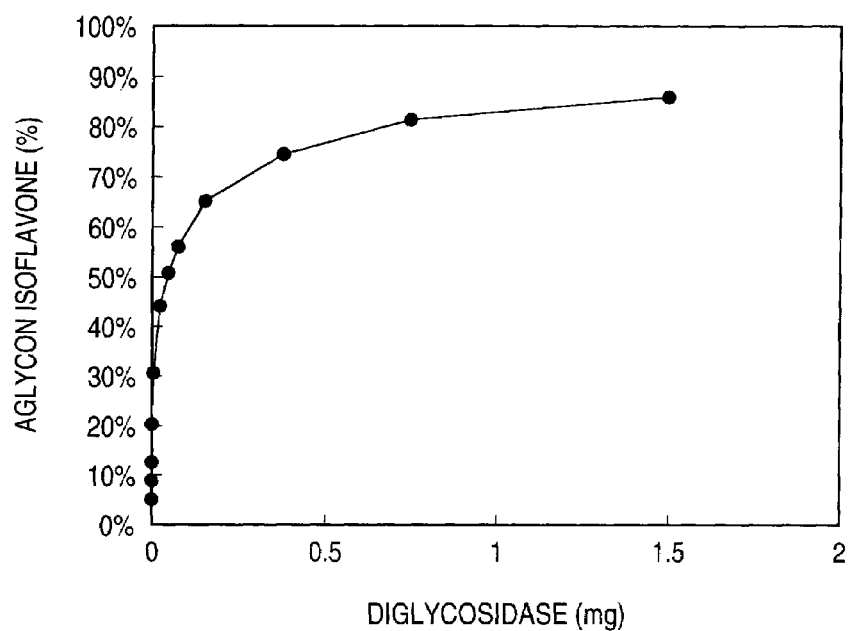
FIG. 3 is a graph showing the results of Example 14.

As described above, the formation of aglycon isoflavones from isoflavone glycosides contained in soy flour was investigated after the reaction at pH 5 and 37° C. for 30 minutes on the assumption of the environment in a stomach. As a result, as shown in Table 43 and FIG. 3, 80% or more of the isoflavone glycosides could be converted into aglycon isoflavones. This result suggests that aglycon isoflavones may be formed from isoflavone glycosides in a stomach when diglycosidase is orally administered.

TABLE 43

Relationship between added amount of diglycosidase and formation (%) of aglycon isoflavones

| diglycosidase | aglycon isoflavones (%) |
|---|---|
| 1.500 | 86.1% |
| 0.750 | 81.3% |
| 0.374 | 74.7% |
| 0.150 | 65.4% |
| 0.075 | 56.3% |
| 0.050 | 51.1% |
| 0.025 | 44.3% |
| 0.010 | 31.0% |
| 0.005 | 20.3% |
| 0.002 | 12.8% |
| 0.001 | 9.2% |
| 0 | 5.0% |

EXAMPLE 15

Formation of Aglycon Isoflavones from an Isoflavone Preparation by Diglycosidase at the pH in a Stomach Into 100 mL of 50 mM acetate buffer (pH 5) was suspended 150 mg of an isoflavone preparation (manufactured by Nature's Bountry, USA). To 3 mL of the suspension was added 0, 0.00045, 0.00113, 0.00225, 0.0045, 0.009, 0.0225, 0.045, 0.09, 0.18, 0.45, or 0.9 mg of diglycosidase (290 AU/g), followed by incubation under shaking at 37° C. for 30 minutes. After the reaction, 10 mL of methanol was added thereto, and aglycon isoflavones were extracted and analyzed by HPLC.

Figure 4:
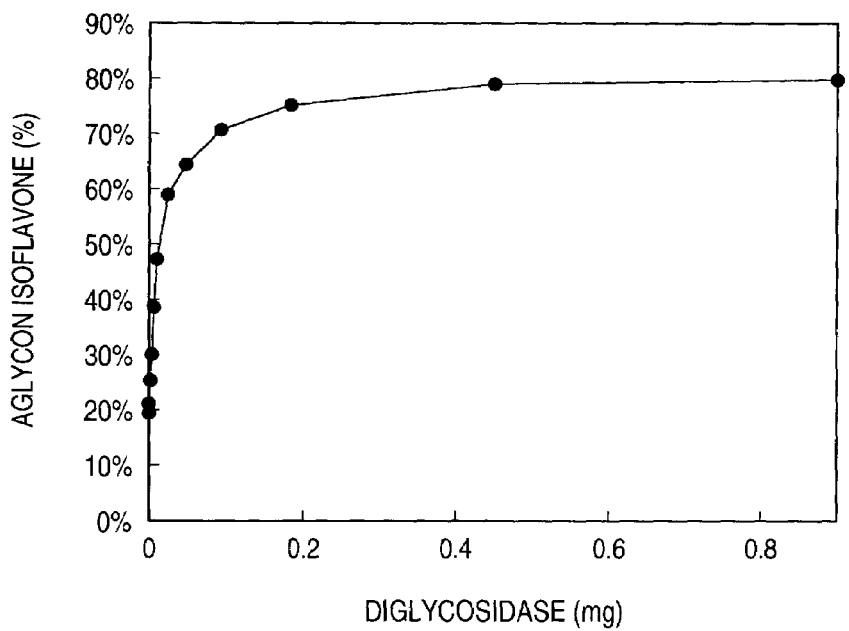
FIG. 4 is a graph showing the results of Example 15.

As described above, the formation of aglycon isoflavones from isoflavone glycosides contained in the isoflavone preparation was investigated after the reaction at pH 5 and 37° C. for 30 minutes on the assumption of the environment in a stomach. As a result, as shown in Table 44 and FIG. 4, 80% or more of the isoflavone glycosides could be converted into aglycon isoflavones. This result suggests that aglycon isoflavones may be formed from isoflavone glycosides in a stomach when diglycosidase is orally administered.

TABLE 44

Relationship between added amount of diglycosidase and formation (%) of aglycon isoflavones

| diglycosidase (mg) | aglycon isoflavones (%) |
|---|---|
| 0.90000 | 79.4% |
| 0.45000 | 78.7% |
| 0.18000 | 75.3% |
| 0.09000 | 70.7% |
| 0.04500 | 64.6% |
| 0.02250 | 59.2% |
| 0.00900 | 47.5% |
| 0.00450 | 38.9% |
| 0.00225 | 30.3% |
| 0.00113 | 25.6% |
| 0.00045 | 21.5% |
| 0.00000 | 20.0% |

INDUSTRIAL APPLICABILITY

A physiologically active substance of aglycon type can be efficiently produced, without resort to any acid/alkali treatment or fermentation and substantially without changing the physical properties of a material.

Since diglycosidase has a nature of well acting on 6"-O-acetyl and 6"-O-malonylglucosides which are resistant to decomposition by conventional glucosidase, the process can be conducted at one-step without requiring the process of converting decomposition-resistant isoflavone glycosides into isoflavone glycosides decomposable by glucosidase, the process being described in JP-A-10-117792. Moreover, the present process hardly causes change of physical properties of a starting material derived from decomposition of proteins or phospholipids, the decomposition being caused during the process of hydrolysis with a strong acid. Furthermore, by using diglycosidase and/or a specific enzyme preparation, the aglycon content in a protein or protein-containing food can be increased and also the flavor thereof can be improved.

The invention claimed is:

1. A process for producing an aglycon which comprises forming an aglycon by treating, with diglycosidase, a glycoside containing an isoflavone as the aglycon,
    wherein said diglycosidase has activity to act upon a disaccharide glycoside to release saccharides in a disaccharide unit,
    wherein said diglycosidase is isolated from a micoroorganism,
    wherein said diglycosidase is not inhibited by free glucose,
    wherein said diglycosidase has an optimum temperature of about 55° C.,
    wherein said diglycosidase has an optimum pH of about 3.5–5, and
    wherein the diglycosidase is diglycosidase produced by *Penicillium multicolor* IAM 7153 or a mutant strain thereof.

2. The process for producing an aglycon according to claim 1, wherein the glycoside containing an isoflavone as the aglycon is one or more selected from the group consisting of daidzin, genistin, or glycitin and acetyl derivatives, succinyl derivatives, or malonyl derivatives thereof.

3. The process for producing an aglycon according to claim 1, wherein the diglycosidase is diglycosidase produced by *Penicillium multicolor* IAM 7153.

4. A method of converting a physiologically active substance of glycoside type into a physiologically active substance of aglycon type, which comprises treating the physiologically active substance of glycoside type with diglycosidase,
    wherein said physiologically active substance of glycoside type comprises an isoflavone as the aglycon,
    wherein said diglycosidase has activity to act upon a disaccharide glycoside to release saccharides in a disaccharide unit,
    wherein said diglycosidase is isolated from *Penicillium multicolor* IAM 7153 or a mutant strain thereof,
    wherein said diglycosidase is not inhibited by free glucose,
    wherein said diglycosidase has an optimum temperature of about 55° C., and
    wherein said diglycosidase has an optimum pH of about 3.5–5.

5. A process for producing a composition rich in a phytogenic physiologically active substance of aglycon type, which comprises treating a phytogenic material containing a phytogenic physiologically active substance of glycoside type with diglycosidase, wherein the phytogenic physiologically active substance of glycoside type comprises an isoflavone as the aglycon,
  wherein said diglycosidase has activity to act upon a disaccharide glycoside to release saccharides in a disaccharide unit,
  wherein said diglycosidase is isolated from *Penicillium multicolor* IAM 7153 or a mutant strain thereof,
  wherein said diglycosidase is not inhibited by free glucose,
  wherein said diglycosidase has an optimum temperature of about 55° C., and
  wherein said diglycosidase has an optimum pH of about 3.5–5.

6. A process for producing an aglycon which comprises forming an aglycon by treating, with diglycosidase, a glycoside containing an isoflavone as the aglycon, wherein said diglycosidase has activity to act upon a disaccharide glycoside to release saccharides in a disaccharide unit, and
  wherein said diglycosidase is prepared by a process comprising:

a) culturing *Penicillium multicolor* IAM 7152 or a mutant strain thereof in a nutrient medium under aerobic conditions with a pH from 3–8 to effect production of said diglycosidase in a culture mixture;

b) isolating said diglycosidase by a combination of centrifugation, ultrafiltration concentration, and salting out of said diglycosidase by 50 to 80% ammonium sulfate from said culture mixture to produce an isolate diglycosidase fraction; and c) purifying said diglycosidase from said isolated diglycosidase fraction by hydrophobic chromatography.

* * * * *